(12) United States Patent
Notte, IV

(10) Patent No.: US 7,804,068 B2
(45) Date of Patent: Sep. 28, 2010

(54) DETERMINING DOPANT INFORMATION

(75) Inventor: John A. Notte, IV, Gloucester, MA (US)

(73) Assignee: ALIS Corporation, Peabody, MA (US)

( * ) Notice: Subject to any disclaimer, the term of this patent is extended or adjusted under 35 U.S.C. 154(b) by 198 days.

(21) Appl. No.: 11/853,471

(22) Filed: Sep. 11, 2007

(65) Prior Publication Data

US 2008/0111069 A1 May 15, 2008

(51) Int. Cl.
*H01J 37/26* (2006.01)
(52) U.S. Cl. .................. 250/309; 250/306; 250/307; 250/492.1; 250/492.3
(58) Field of Classification Search ............. 250/306, 250/307, 309, 281, 282, 288, 492.1, 492.2, 250/492.21, 492.3
See application file for complete search history.

(56) References Cited

U.S. PATENT DOCUMENTS

| | | | |
|---|---|---|---|
| 2,893,624 A | 7/1959 | Fricke | |
| 3,121,155 A | 2/1964 | Berry | |
| 3,602,710 A | 8/1971 | Mueller | |
| 3,777,211 A | 12/1973 | Kuijpers | |
| 3,868,507 A | 2/1975 | Panitz | |
| 3,889,115 A * | 6/1975 | Tamura et al. | 850/43 |
| 4,044,255 A | 8/1977 | Krisch et al. | |
| 4,117,322 A * | 9/1978 | McKinney | 850/9 |
| 4,139,773 A | 2/1979 | Swanson | |
| 4,236,073 A | 11/1980 | Martin | |
| 4,255,661 A | 3/1981 | Liebl | |
| 4,352,985 A | 10/1982 | Martin | |
| 4,451,737 A | 5/1984 | Isakozawa | |
| 4,467,240 A | 8/1984 | Futamoto et al. | |
| 4,629,898 A | 12/1986 | Orloff | |
| 4,633,084 A | 12/1986 | Gruen et al. | |
| 4,638,209 A | 1/1987 | Asamaki et al. | |
| 4,639,301 A | 1/1987 | Doherty et al. | |
| 4,649,316 A | 3/1987 | Cleaver et al. | |
| 4,721,878 A | 1/1988 | Hagiwara et al. | |
| 4,774,414 A | 9/1988 | Umemura et al. | |
| 4,785,177 A | 11/1988 | Besocke | |
| 4,874,947 A | 10/1989 | Ward et al. | |
| 4,954,711 A | 9/1990 | Fink et al. | |
| 4,983,540 A | 1/1991 | Yamaguchi et al. | |
| 4,983,830 A * | 1/1991 | Iwasaki | 850/1 |
| 4,985,634 A | 1/1991 | Stengl et al. | |

(Continued)

FOREIGN PATENT DOCUMENTS

DE 196 04 272 8/1996

(Continued)

OTHER PUBLICATIONS

Jiang et al., "In situ ion channeling study of gallium disorder and gold profiles in Au-implanted GaN," J. App. Physics, 87(11):7671-7678, (2000).

(Continued)

*Primary Examiner*—Jack I Berman
*Assistant Examiner*—Nicole Ippolito Rausch
(74) *Attorney, Agent, or Firm*—Fish & Richardson P.C.

(57) ABSTRACT

Methods that include using a noble gas ion beam to determine dopant information for a sample are disclosed, the dopant information including dopant concentration in the sample, dopant location in the sample, or both.

26 Claims, 15 Drawing Sheets

U.S. PATENT DOCUMENTS

| | | | |
|---|---|---|---|
| 5,034,612 A | 7/1991 | Ward et al. |
| 5,059,785 A | 10/1991 | Doyle et al. |
| 5,063,294 A | 11/1991 | Kawata et al. |
| 5,083,033 A | 1/1992 | Komano et al. |
| 5,093,572 A | 3/1992 | Hosono |
| 5,151,594 A | 9/1992 | McClelland |
| 5,188,705 A | 2/1993 | Swanson et al. |
| 5,324,950 A | 6/1994 | Otaka et al. |
| 5,414,261 A | 5/1995 | Ellisman et al. |
| 5,502,306 A | 3/1996 | Meisburger et al. |
| 5,574,280 A | 11/1996 | Fujii et al. |
| 5,750,990 A | 5/1998 | Mizuno et al. |
| 5,783,830 A | 7/1998 | Hirose et al. |
| 5,916,424 A | 6/1999 | Libby et al. |
| 5,976,390 A | 11/1999 | Muramatsu |
| 5,986,270 A | 11/1999 | Bormans et al. |
| 6,028,953 A | 2/2000 | Nakamura et al. |
| 6,042,736 A | 3/2000 | Chung |
| 6,042,738 A | 3/2000 | Casey et al. |
| 6,211,527 B1 | 4/2001 | Chandler |
| 6,268,608 B1 | 7/2001 | Chandler |
| 6,354,438 B1 | 3/2002 | Lee et al. |
| 6,395,347 B1 | 5/2002 | Adachi et al. |
| 6,414,307 B1 | 7/2002 | Gerlach et al. |
| 6,504,151 B1 | 1/2003 | Mitchell et al. |
| 6,538,254 B1 | 3/2003 | Tomimatsu et al. |
| 6,576,894 B1 | 6/2003 | Doong |
| 6,579,665 B2 | 6/2003 | Lee et al. |
| 6,581,023 B1 | 6/2003 | Kim |
| 6,700,122 B2 | 3/2004 | Matsui et al. |
| 6,727,500 B1 | 4/2004 | Berger et al. |
| 6,753,535 B2 | 6/2004 | Rose |
| 6,791,084 B2 | 9/2004 | Shimoma et al. |
| 6,822,245 B2 | 11/2004 | Muto et al. |
| 6,833,719 B2 | 12/2004 | Hasegawa et al. |
| 6,875,981 B2 | 4/2005 | Nishikawa |
| 7,084,399 B2 | 8/2006 | Muto et al. |
| 7,119,333 B2 | 10/2006 | Herschbein et al. |
| 7,230,244 B2 | 6/2007 | Trotz et al. |
| 7,321,118 B2 | 1/2008 | Ward |
| 7,368,727 B2 | 5/2008 | Ward |
| 7,414,243 B2 | 8/2008 | Ward |
| 7,485,873 B2 | 2/2009 | Ward et al. |
| 7,488,952 B2 | 2/2009 | Ward et al. |
| 7,495,232 B2 | 2/2009 | Ward et al. |
| 7,504,639 B2 | 3/2009 | Ward et al. |
| 7,511,279 B2 | 3/2009 | Ward et al. |
| 7,511,280 B2 | 3/2009 | Ward et al. |
| 7,518,122 B2 | 4/2009 | Ward et al. |
| 7,521,693 B2 | 4/2009 | Ward et al. |
| 7,554,096 B2 | 6/2009 | Ward et al. |
| 7,554,097 B2 | 6/2009 | Ward et al. |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 2002/0134949 A1 | 9/2002 | Gerlach et al. |
| 2002/0144892 A1 | 10/2002 | Lee et al. |
| 2002/0170675 A1 | 11/2002 | Libby et al. |
| 2003/0062487 A1 | 4/2003 | Hiroi et al. |
| 2003/0098416 A1 | 5/2003 | Shemesh et al. |
| 2003/0122085 A1 | 7/2003 | Stengl et al. |
| 2003/0174879 A1 | 9/2003 | Chen |
| 2003/0219658 A1* | 11/2003 | Shishido et al. ............... 430/30 |
| 2004/0031936 A1 | 2/2004 | Oi et al. |
| 2004/0065826 A1* | 4/2004 | Berger et al. ................. 250/310 |
| 2004/0121069 A1 | 6/2004 | Ferranti et al. |
| 2005/0045821 A1 | 3/2005 | Noji et al. |
| 2005/0178980 A1 | 8/2005 | Skidmore et al. |
| 2005/0279952 A1 | 12/2005 | Ishitani et al. |
| 2006/0060777 A1 | 3/2006 | Motoi et al. |
| 2006/0076494 A1* | 4/2006 | Bloess et al. ............. 250/339.07 |
| 2006/0097166 A1 | 5/2006 | Ishitani et al. |
| 2006/0197017 A1 | 9/2006 | Motoi et al. |
| 2006/0284091 A1 | 12/2006 | Ward |
| 2006/0284092 A1 | 12/2006 | Ward |
| 2007/0025907 A1 | 2/2007 | Rezeq et al. |
| 2007/0051900 A1 | 3/2007 | Ward |
| 2007/0057182 A1 | 3/2007 | Feuerbaum |
| 2007/0138388 A1* | 6/2007 | Ward et al. .................. 250/288 |
| 2007/0158555 A1 | 7/2007 | Ward et al. |
| 2007/0158556 A1 | 7/2007 | Ward et al. |
| 2007/0158557 A1 | 7/2007 | Ward et al. |
| 2007/0158558 A1 | 7/2007 | Ward et al. |
| 2007/0158580 A1 | 7/2007 | Ward et al. |
| 2007/0158581 A1 | 7/2007 | Ward et al. |
| 2007/0158582 A1 | 7/2007 | Ward et al. |
| 2007/0187621 A1 | 8/2007 | Ward et al. |
| 2007/0194226 A1 | 8/2007 | Ward et al. |
| 2007/0194251 A1 | 8/2007 | Ward et al. |
| 2007/0205375 A1 | 9/2007 | Ward et al. |
| 2007/0210250 A1 | 9/2007 | Ward et al. |
| 2007/0210251 A1 | 9/2007 | Ward et al. |
| 2007/0215802 A1 | 9/2007 | Ward et al. |
| 2007/0221843 A1 | 9/2007 | Ward et al. |
| 2007/0227883 A1 | 10/2007 | Ward et al. |
| 2007/0228287 A1 | 10/2007 | Ward et al. |
| 2008/0067385 A1* | 3/2008 | Tokuda et al. ............... 250/310 |
| 2008/0067408 A1 | 3/2008 | Winkler |
| 2008/0111069 A1 | 5/2008 | Notte |
| 2008/0217531 A1 | 9/2008 | Muray |
| 2008/0217555 A1 | 9/2008 | Ward et al. |

FOREIGN PATENT DOCUMENTS

| | | |
|---|---|---|
| DE | 197 15 226 A | 10/1998 |
| DE | 197 44 126 A | 4/1999 |
| EP | 0 225 969 | 6/1987 |
| EP | 0 317 952 | 5/1989 |
| EP | 0 427 532 | 5/1991 |
| EP | 0 477 992 A2 | 4/1992 |
| EP | 0 643 297 | 3/1995 |
| EP | 0 734 045 | 9/1996 |
| EP | 1 491 654 | 12/2004 |
| EP | 1 655 265 | 5/2006 |
| EP | 1 696 219 | 8/2006 |
| EP | 1 746 386 | 1/2007 |
| EP | 2 031 633 | 3/2009 |
| FR | 2244257 A | 4/1975 |
| GB | 1 604 898 | 12/1981 |
| GB | 2 225 156 | 5/1990 |
| JP | 55-126949 | 10/1980 |
| JP | 5209844 | 12/1983 |
| JP | 62 051134 | 3/1987 |
| JP | 63 040241 A | 2/1988 |
| JP | 63 045740 | 2/1988 |
| JP | 63 200434 | 8/1988 |
| JP | 1-130450 | 5/1989 |
| JP | 02 087440 | 3/1990 |
| JP | 03-214554 | 9/1991 |
| JP | 03 276547 | 12/1991 |
| JP | 04 341734 | 11/1992 |
| JP | 04 341743 | 11/1992 |
| JP | 5275050 | 10/1993 |
| JP | 05-297146 | 11/1993 |
| JP | 07045230 | 2/1995 |
| JP | 2789610 | 8/1995 |
| JP | 07-272652 | 10/1995 |
| JP | 2001 176440 | 6/2001 |
| JP | 02 025488 | 1/2002 |
| JP | 2003 302579 A | 10/2003 |
| JP | 04 265629 | 9/2004 |
| JP | 2004 265629 | 9/2004 |
| JP | 2008 270073 | 11/2008 |

| WO | 98/47172 | 10/1998 |
| WO | 2001/04611 | 1/2001 |
| WO | WO 01/59806 | 8/2001 |
| WO | WO 2004/015496 | 2/2004 |
| WO | WO 2004/044596 | 5/2004 |
| WO | 2004/068538 | 8/2004 |
| WO | 2006/133241 | 12/2006 |

OTHER PUBLICATIONS

Puranik and King, "Sputter depth profiling of thin films with LEIS and LENRS," Applied Surface Science, 28(2):180-186, (1987).

Bernatskii and Pavlov, "Field Desorption of a Potassium-Gold Film on Tungsten," Physics of the Solid State, 46(8):1538-1541, 2004.

Boerret et al., "Long time current stability of a gas filed ion source with a supertip," J. Phys. D. Appl. Phys. 21(12):1835-1837, 1988.

Giannuzzi and Stevie, *Introduction to Focused Ion Beams—Instrumentation, Theory, Techniques and Practice*, Nov. 2004, Springer, XP002442742, Chapter 3, see especially p. 56, second section.

Giannuzzi and Stevie, *Introduction to Focused Ion Beams—Instrumentation, Theory, Techniques and Practice*, Nov. 2004, Springer, XP002462691, Chapter 5—Device Edits and Modifications.

Golubev et al., "Field Emission Study of the Growth of Close-Packed and Stepped Surfaces of a Tungsten Single Crystal," J. Crystal Growth 52:48-52, 1981.

Hiroshima et al., "A focused He+ ion beam with a high angular current density," Jpn. J. Appl Phys., 31(1)(12B):4492-4495, 1992.

Kuo et al., "Noble Metal/W(111) Single-Atom Tips and Their Field Electron and Ion Emission Characteristics," Jpn. J. App. Phy., 45(11):8972-8983, 2006.

Kubena et al., "A low magnification focused ion beam system with 8 nm spot size," J. Vac. Sci. Technol., 9(6):3079-3083, 1991.

Liu and Orloff, "Analytical model of a gas phase filed ionization source," J. Vac. Sci. Technol. B 23(6):2816-2820, 2005.

Melngailis, "Focused ion beam Lithography", Nuclear Instr. And Methods in Phys. Res. B80(81):1271-1280, 1993.

Pavlov, "Atomically Sharp <111> Trihedral Angle of a Tungsten Tip," Physics of a Solid State, 49(8):1579-1582, 2007.

Pavlov, "Field-Desorption Microscopy Study of the Deformation of a Tungsten Tip Subjected to Thermal Treatment in an Electric Field," Physics of the Solid State, 47(11):2180-2185, 2005.

Pavlov, "Field Desorption Microscopy of the <111> Trihedral Angle of a Reconstructed Tungsten Tip," Technical Physics, 51(9):1210-1214, 2006.

Pavlov, "Observation of the Drawing out of Needles by Electric Fields," A translation of JETP Pis'ma v Redaktsiyu of the Academy of Sciences of the USSR, 17(5):177-179, 1973.

Pavlov, "Variations in Shapes of Outgrowths on a Tungsten Tip during Growth in an Electric Field," Physics of a Solid State, 48(5):969-972, 2006.

Sakai et al., "Contrast mechanisms in scanning ion microscope imaging for metals," App. Phys. Letters, AIP, vol. 73, No. 5, pp. 611-613, Aug. 3, 1998.

Sakata et al., "Helium field ion source for application in a 100 keV focused ion beam system," J. Vac. Sci. Technol. B 10(6):2842-2845, 1992.

Sendecki and Barwinski, "A scanning field emission microscope," Meas. Sci. Technol., 6(3):306-309, (1995).

Unger et al., "Probe hole field electron/field ion microscopy and energy spectroscopy of ultrasharp [111]-oriented tungsten tips," Applied Surface Science 87(88):45-52, 1995.

Vlasov et al., "High-temperature filed evaporation of thermofield microscopic protuberances," Sov. Tech. Phys. Lett. 12(5):224-225, 1986.

Ward et al., "Focused Ion Beam Induced Optical Emission Spectroscopy," J. Vac. Sci. Technol. 6(6):2100-2103, 1988.

Nova 600 Nanolab Product Data, Fei Company Product Data, 2003, XP007903648.

Breguet and Clavel, "Stick and Slip Actuators: design, control, performances and applications," Micromechatronics and Human Science, Proceedings of the 1998 International Symposium, 89-95, 1998.

Fu et al., "Microfabrication of microlens array by focused ion beam technology," Microelectronic Engineering, 54(3-4):211-221, 2000.

Liu and Wang, "A self-moving precision positioning stage utilizing impact force of spring-mounted piezoelectric actuator," Sensors and Actuators, 102(1-2):83-92, 2002.

Nomura et al., "Application of Electromagnetic Actuator using Rubber Film to Three-Degrees-of-Freedom Precision Stage," Advanced Intelligent Mechatronics (AIM 2003), 101-106, 2003.

Orloff et al., "High Resolution Focused Ion Beams: FIB and its Applications," Review of Scientific Instruments, 136-145, 2003.

Orloff et al, "Fundamental limits to imaging resolution for focused ion beams," J. Vacuum Science & Tech., 14(6):3759-3763, 1996.

Versteyhe et al., "A rigid and accurate piezo-stepper based on smooth learning hybrid force-position controlled clamping," Proceedings of the 1998 IEEE International Conference on Robotics & Automation, 4:3059-3064, 1998.

"An Introduction to the Helium Ion Microscope" (Materials Research Society Meeting, Nov. 2006).

Bell, A.E. et al., "High-field ion sources", Rev. Sci. Instrum. 61(1): 363-365 (1990).

Binh, V.T., "In situ fabrication and regeneration of microtips for scanning tunneling microscopy", J. Microscopy 152(2): 355-361 (1988).

Breese et al., "Ion optical study of a transmission ion microscope," Muclear instruments & Methods in Physics Research, Section-B: Beam Interactions with Materials and Atoms, Elsevier, Amsterdam, NL, vol. 158, No. 1-4, Sep. 2, 1999, pp. 236-240.

Brune et al., "Surface migration of "hot" adatoms in the course of dissociative chemisorption of oxygen on Al(111)," Phys. Rev. Lett. 68, Issue 5-3 Feb. 1992, pp. 624-626.

Bunday et al., "Determination of optimal parameters for CD-SEM measurement of line-edge roughness," Metrology, Inspection, and Process Control for Microlithography XVIII, Proceedings of SPIE—The International Society for Optical Engineering, vol. 5375, pp. 515-533, May 24, 2004.

Butz et al., "From Micro- to Nanoprobes: Auspices and Horizons," Nuclear Intruments & Methods in Physics Research, Section—B: Beam Interactions with Materials and Atoms, Elsevier, Amsterdam, NL, vol. 113, No. 1, Jun. 1996, pp. 317-322.

Edinger, K. et al., "Development of a high brightness gas field ion source", J. Vac. Sci. Technol. B 15(6): 2365-2368 (1997).

Escovitz et al., "Scanning Transmission Ion Microscope with a Field Ion Source," Feb. 24, 1975, Proceedings of the National Academy of the Sciences, vol. 72, No. 5, Published May 1975, pp. 1826-1828.

Fink et al., "Atomic Resolution in Lensless Low-energy Electron Holography," Phys. Rev. Lett. 67, Issue 12-16 Sep. 1991, pp. 1543-1546.

Fink et al., "Coherent point source electron beams," Journal of Vacuum Science & Technology B: Microelectronics and Nanometer Structures, Nov. 1990, vol. 8, Issue 6, pp. 1323-1324.

Fink et al., "Lattice Steps and Adatom Binding on Tungsten (211)," Surf. Sci., vol. 143, No. 1, pp. 125-144, Jul. 1984.

Fink, H.-W. et al., "Electron and Ion Microscopy Without Lenses", Nanostructures and Quantum Effects (Springer-Verlag, 1994), pp. 17-27.

Fink, H.-W., "Mono-atomic tips for scanning tunneling microscopy", IBM J. Res. Develop. 30: 460-465 (1986).

Fink, H.-W., "Point Source for Ions and Electrons", Physica Scripta 38: 260-263 (1988).

Fotino, M., "Tip sharpening by normal and reverse electrochemical etching", Rev. Sci. Instrum. 64(1): 159-167 (1993).

Fu, T.-Y. et al., "Method of creating a Pd-covered single-atom sharp W pyramidal tip: Mechanism and energetics of its formation", Phys. Rev. B 64: 113401-1-4 (2001).

Grivet et al., "Ion Microscopy: History and Actual Trends," Ann NY Acad Sci, 1978 NY Acad of Sci, vol. 306, Feb. 23, 1977, pp. 158-182.

Hill, R. et al., "The ALIS He Ion Source and its Application to High Resolution Microscopy" (Seventh International Conference on Charged Particle Optics, Jul. 2006).

Hong-Shi Kuo et al., "Preparation and characterization of single-atom tips," Nano Letters, vol. 4, No. 12, pp. 2379-2382, Dec. 2004.

Horch, S. et al., "Field emission from atomic size sources", J. Appl. Phys. 74(6): 3652-3657 (1993).

Horiuchi, K. et al., "Emission characteristics and stability of a helium field ion source", J. Vac. Sci. Technol. B. 6(3): 937-940 (1988).

Itakura et al., "Focusing Column For Helium Field Ion Source," Microelectric Engineering, Elsevier Publishers BV., Amsterdam, NL, vol. 3, No. 1-4, pp. 153-160, Sep. 23, 1985.

Itakura et al., "Microprobe of Helium Ions," Journal of Vacuum Science and Technology: Part B, AVS / AIP, Melville, New York, NY, vol. 9, No. 5, pp. 2596-2601, Sep. 1, 1991.

J. Meingailis, "Ion Sources for Nanofabrication & High Resolution Lithography," IEEE Proceedings of the 2001 Particle Accelerator Conference, Chicago, Illinoise, (2002).

Jasic et al., "New Developments in IBIC for the Study of Change Transport Properties of Radiation Detector Materials," Nuclear Instruments & Methods in Physics Research, Section—B: Beam Interactions with Materials and Atoms, Elsevier, Amsterdam, NL, vol. 158, No. 1-4, Sep. 2, 1999, pp. 458-463.

K. Jousten et al. "Growth & Current Charities of a Stable field Ion Emitter," Ultramicroscope 26, pp. 301-312 (1988).

Kalbitzer et al., "High-brightness source for ion and electron beams (invited)," Review of Scientific Instruments, American Institute of Physics, vol. 69, No. 2, pp. 1026-1031, Feb. 2, 1998.

Kalbitzer et al., "Ion beam modification for submicron technology," Nuclear Instruments & Methods in Physics Research, Section—B: Beam Interations With Materials and Atoms, Elsevier, Amsterdam, NL, vol. 113, No. 1, pp. 154-160, Jun. 1996.

Kalbitzer et al., "Multipurpose nanobeam source with supertip emitter," Journal of Vacuum Science & Technology B: Microelectronics Processing and Phenomena, American Vacuum Society, vol. 16, No. 4, pp. 2455-2461, Jul. 1998.

Kim et al., "Effects of low-energy (1-1.5 kV) nitrogen-ion bombardment on sharply pointed tips: Sputtering, implantation, and metal-nitride formation," Journal of Applied Physics, American Institute of Physics, Vol. 81, No. 2, p. 944, Jan. 15, 1997.

Levi-Setti, "High Resolution Scanning Ion Probes: Application to Physics and Biology," Nuclear Instruments and Methods, North-Holland, vol. 168, No. 1-3, pp. 139-149, Jun. 25, 1979.

Levi-Setti, "Proton Scanning Microscopy: Feasiblity and Promise," Scanning Electron Microscopy. Proceedings of the Annual Scanning Electron Microscope Symposium, Chicago, IL., pp. 125-134, Apr. 11, 1974.

Liu et al., "A Study of Optical Properties of Gas Phase Field Ionization Sources," Advances in Imagin and Electron Physics, Elsevier Academic Press, vol. 138, pp. 147-175, Oct. 2005.

Lucier, A.-S., "Preparation and Characterization of Tungsten Tips Suitable for Molecular Electronics Studies", excerpts from MSc Thesis, McGill University, 2004.

Magnan, "The Proton Microscope," Nucleonics, vol. 4, No. 4, Apr. 1949, pp. 52-66.

McGuinness, P.E., "Seeing at Atomic Resolution is Believing: Welcome the Helium Ion Microscope", Scanning 27(6): 323 (2005).

Melngailis, J., "Focused ion beam technology and applications", J. Vac. Sci. Technol. B 5(2): 469-495 (1987).

Morgan, J. et al., "An Introduction to the Helium Ion Microscope" (Microscopy Today, Jul. 2006).

Muller, H.U. et al., "Emission properties of electron point sources", Ultramicroscopy 50: 57-64 (1993).

Mutsaers, "Nuclear Microprobe Design," Nuclear Instruments & Methods in Physics Research, Section—B: Beam Interactions with Materials and Atoms, Elsevier, Amsterdam, NL, vol. 113, No. 1, Jun. 1996, pp. 323-329.

Notte, J. et al., "An Introduction to Helium Ion Microscopy" (Microscopy and Micro-Analysis, Jul. 2006).

Notte, J. et al., "Sample Interaction and Contrast Mechanisms of the Helium Ion Microscope" (Scanning Conference, Apr. 2006).

Orloff et al., "A Scanning Ion Microscope with A Field Ionization Source," Scanning Electron Microscopy. Proceedings of the Annual Scanning Electron Microscope Symposium, Chicago, IL, No. 10, pp. 57-62, Mar. 1977.

Orloff et al., "High-Resolution Focused Ion Beams: FIB and its Applications," Kluwer Academic / Plenum Publishers, New York, Chapter 6.8, (2003).

Orloff, " High-Resolution Focused Ion Beams," Review of Scientific Instruments, AIP, vol. 64, No. 5, pp. 1106-1107, May 1, 1993.

Purcell et al., "Characterization of atomic-size metal ion sources," Journal of Vacuum Science & Technology B: Microelectronics and Nanometer Structures, Jan. 2001, vol. 19, Issue 1, pp. 79-86.

Qing Ji, "Maskless, Resistless Ion Beam Lithography Process," Ph.D. Dissertation, Department of Electrical Engineering and Computer Sciences, UCAL Berkeley (2003).

Rezeq, M. et al., "Sharpening of a Field of Ion Microscope (FIM) Tungsten Tip by the Controlled Interation of Nitrogen with the Tip Surface Atoms," Abastract from APS March Meeting (2004).

Russell P.E. et al., "Chemically and geometrically enhanced focused ion beam micromachining," Journal of Vacuum Science and Tehcnology B, vol. 16, No. 4, Jul./Aug. 1998, 2494-2498.

Schmid et al., "In-line holography using low-energy electrons and photons: Applications for manipulation on a nanometer scale," Journal of Vacuum Science & Technology B: Microelectronics and Nanometer Structures, Nov. 1995, vol. 13, Issue 6, pp. 2428-2431.

Schmid et al., "Mechanical and electronic manipulation of nanometer-sized wires," Nanotechnology, vol. 5, pp. 26-32, 1994.

Schmid, H. et al., "Combined electron and ion projection microscopy", Appl. Surf. Sci. 67: 436-443 (1993).

Stevie et al., "Focused Ion Beam Gases for Deposition and Enhanced Etch," Chapter 3 of Introduction to Focused Ion Beams—Instrumentation, Theory, Techniques and Practice, Edited by Giannuzi et al., Published by Springer, pp. 53-72, (2005).

Stocker, W. et al., "Low-energy electron and ion projection microscopy", Ultramicroscopy 31: 379-384 (1989).

Thompson et al., "Towards a commercial gas field ion source," Proceedings of SPIE, vol. 2437.

Tondare et al., "The concept of a high-brightness, miniaturized gas field ion source," Vacuum Microelectronics Conference, 2003. Technical Digest of the 16th International IEEE, pp. 307-308, Jul. 7, 2003.

Tondare V. N., "Quest for high brightness, monochromatic noble gas ion sources," J.Vac.Sci.Technol., A 23, 1498 (2005).

Valdiviez et al., "The mechanical design of a proton microscope for radiography at 800 MeV,"Institute of Electrical and Electronics Engineers: Proceedings of the 2003 Particle Accelerator Conference. PAC 2003. Portland, OR, May 12-16, 2003, Particle Accelerator Conference, New York, NY: IEEE, US. vol. 1 of 5, May 12, 2003.

Ward, B.W. et al., "The Helium Ion Microscope: A New Tool for Nanoscale Microscopy and Metrology" (Electron, Ion, and Photon Beam Nanotechnology Conference, May 2006).

Wengelnik, H. et al., "Oxygen-induced sharpening process of W(111) tips for scanning tunneling microsope use," J. Vac. Sci. Technol. A 8(1): 438-440 (1990).

Wilbertz et al., "Recent Progress in gas field ion source technology," Proceeding of SPIE, vol. 2194.

Wolf et al., "Design and performance of a scanning probe-hole field emission microscope," Surface Science, vol. 246, No. 1-3, pp. 420-427, Apr. 1991.

Doyle et al., "A new approach to nuclear microscopy: the ion-electron emission microscope," Nuclear Instruments & Methods in Physics Research B 158 (1999) pp. 6-17.

Hanson et al., "H2 and rare gas field ion source with high angular current," J Vacuum Science and Technology, 16(6) Nov./Dec. 1979, pp. 1875-1878.

Marquardt et al., "Cryogenic Material Properties Database," $11^{th}$ International Cryocooler Conference, Jun. 20-22, 2000, Keystone, CO.

Tomaru et al., "Thermal lensing in an cryogenic sapphire substrates," Class. Quantum Grav. 19 (2002), pp. 2045-2049.

Reyntjens and Puers, "A review of focused ion beam applications in microsystem technology," J. Micromech. Microeng., 11(4):287-300, 2001.

Kalbitzer, "Bright ion beams for the nuclear microprobe," Nuclear Instruments & Methods In Physics Research, Section—B: Beam Interactions With Materials And Atoms, Elsevier, Amsterdam, NL., vol. 158, No. 1-4, pp. 53-60, Sep. 2, 1999.

Notte, J.A. et al., "An Introduction to Helium Ion Microscopy and its Nanotechnology Applications" (NanoScience and Technology Institute, May 2006).

Shrednik et al., "Growth of Tips in the Directions Normal to Close-Packed Faces by Heating in the Presence of an Electric Field," Phys. Stat. Sol. (a), 23(1):373-381, 1974.

Li and Rau, "Magnetic domain structures of focused ion beam-patterned cobalt films using scanning ion microscopy with polarization analysis," 95(11):6527-6529, (2004).

Wouters et al., "Instrumentation and experimental procedure for investigation of the electronic and geometrical structure of metal surfaces," Meas. Sci. Technol. 1:41-49, (1990).

Chakk and Horvitz, "Contribution of dynamic charging effects into dopant contrast mechanisms in silicon," J. Mater. Sci., 41(14):4554-4560, 2006.

International Technology Roadmap for Semiconductors, 1-36, 2003.

Rubin and Poate, "Ion Implantation in Silicon Technology," Am. Inst. Of Physics, 12-15, 2003.

Venables et al., "Secondary electron imaging as a two-dimensional dopant profiling technique: Review and update," J. Vac. Sci. Technol. B, 16(1):362-2366, 1998.

International Preliminary Report on Patentability for international application No. PCT/US2008/074143 dated Mar. 25, 2010.

Fu et al., "Characterization of focused ion beam induced deposition process and parameters calibration," Sensors and Actuators, 88(1):58-66, 2001.

* cited by examiner

DETERMINING DOPANT INFORMATION

TECHNICAL FIELD

This disclosure relates to ion sources, systems, and methods.

BACKGROUND

Ions can be formed using, for example, a liquid metal ion source or a gas field ion source. In some instances, ions formed by an ion source can be used to determine certain properties of a sample that is exposed to the ions, or to modify the sample. In other instances, ions formed by an ion source can be used to determine certain characteristics of the ion source itself.

SUMMARY

In a first aspect, the disclosure features a method that includes using a noble gas ion beam to determine dopant information for a sample, the dopant information including dopant concentration in the sample, dopant location in the sample, or both.

In another aspect, the disclosure features a method that includes combining data from at least two different images of a sample formed by exposing the sample to a noble gas ion beam, where combining the data provides information including dopant location in the sample, dopant concentration in the sample, or both.

In a further aspect, the disclosure features a method that includes comparing reference data for a sample to an image of the sample formed by exposing the sample to a noble gas ion beam to provide information including dopant location in the sample, dopant concentration in the sample, or both.

In another aspect, the disclosure features a method that includes exposing a sample to a noble gas ion beam to cause scattered noble gas particles to leave a surface of the sample, and determining dopant information for the sample based on energies of the scattered noble gas particles, where the dopant information includes information about a dopant concentration at a depth below a surface of the sample, and where the depth is measured in a direction normal to the surface of the sample.

In a further aspect, the disclosure features a method that includes exposing a sample to a noble gas ion beam to cause scattered noble gas particles to leave a surface of the sample, and determining information about a mass of dopant particles in the sample based on energies of the scattered noble gas particles, angular directions of the scattered noble gas particles, or both.

Embodiments can include one or more of the following features.

The noble gas can include helium. Alternatively, or in addition, the noble gas can include neon and/or argon and/or krypton and/or xenon.

The scattered noble gas particles can include noble gas ions. Alternatively, or in addition, the scattered noble gas particles can include neutral noble gas atoms.

The dopant particles can include atoms. Alternatively, or in addition, the dopant particles can include molecules and/or ions and/or molecular fragments and/or other chemical moieties.

Determining dopant information can include measuring an abundance of particles leaving a surface of the sample. The particles can include secondary electrons and/or scattered noble gas ions and/or neutral scattered noble gas atoms. Determining dopant concentration in the sample can include comparing the measured abundance of particles to a standard sample to determine the concentration.

The methods can include measuring energies of particles leaving a surface of the sample, angular directions of particles leaving a surface of the sample, or both. The particles can include scattered noble gas ions and/or neutral scattered noble gas atoms.

The methods can include determining a maximum dimension of a doped region of the sample based on the dopant location information. Determining the maximum dimension can include determining positions of one or more edges of the doped region.

The dopant concentration information can include information about dopant concentration at a depth below a surface of the sample, where the depth is measured along a direction normal to the surface of the sample. Determining dopant concentration at a depth below the surface of the sample can include measuring a plurality of images of the sample, each image including dopant concentration information. Each image of the plurality of images can correspond to a different noble gas ion beam energy.

Determining dopant concentration at a depth below the surface of the sample can include measuring one or more images of the sample, where at least one image of the sample corresponds to a non-zero angle of incidence of the noble gas ion beam with respect to the surface normal.

The methods can include determining a mass of dopant particles. Determining a mass of the dopant particles can include measuring an energy and an angle of scattered noble gas particles leaving a surface of the sample. Dopant concentration at a depth below the surface of the sample can be determined from the measured energies of scattered noble gas particles. The methods can include determining a composition of the dopant particles based on the mass.

The methods can include measuring at least one image of the sample, and identifying dopant particles that occupy interstitial sites within a crystal structure of the sample.

The methods can include measuring a plurality of images of the sample, where each image is measured at a different noble gas ion energy.

The methods can include measuring a plurality of images of the sample, where each image is measured by a charged particle detector, and each image corresponds to a different electric potential difference between an electrode of the detector and the sample.

The methods can include exposing the sample to an electron beam during determination of at least some of the dopant information.

The noble gas ion beam can have a spot size with a dimension of 10 nm or less at a surface of the sample. The noble gas ion beam can have an ion beam current at a surface of the sample of one nA or less. The ion beam current at the surface of the sample can be 0.1 fA or more. The noble gas ion beam can have an energy spread at a surface of the sample of five eV or less.

The noble gas ion beam can have a reduced etendue of $1\times10^{-16}$ cm$^2$srV or less. The noble gas ion beam can have an etendue of $5\times10^{-21}$ cm$^2$sr or less. The noble gas ion beam can have a reduced brightness at a surface of the sample of $5\times10^8$ A/m$^2$srV or more. The noble gas ion beam can have a convergence half angle of 5 mrad or less at a surface of the sample.

The methods can include measuring at least one image of the sample, where the image of the sample has a resolution of three nm or less.

A first image of the at least two different images can be formed by exposing the sample to noble gas ions at a first ion beam current, and a second image of the at least two different images can be formed by exposing the sample to noble gas ions at a second ion beam current.

Each of the at least two different images can be formed by measuring particles leaving a surface of the sample using a charged particle detector. A first image of the at least two different images can correspond to a first electric potential difference between an electrode of the charged particle detector and the sample, and a second image of the at least two different images can correspond to a second electric potential difference between the electrode and the sample.

The noble gas ion beam can form an angle of incidence relative to a normal to a surface of the sample, and at least one image of the at least two different images can correspond to a non-zero angle of incidence of the noble gas ion beam.

A first image of the at least two different images can be formed by exposing the sample to noble gas ions at a first ion energy, and a second image of the at least two different images can be formed by exposing the sample to noble gas ions at a second ion energy.

A first image of the at least two different images can correspond to secondary electrons leaving a surface of the sample, and a second image of the at least two different images can correspond to scattered noble gas ions leaving the surface of the sample.

The methods can include measuring distances between at least some of the dopant locations and a reference location on a surface of the sample.

Dopant concentration information can include information about dopant concentration at a surface of the sample.

The dopant concentration information can be derived by comparing the combined data to data from a standard sample.

The methods can include measuring a plurality of energies of scattered noble gas particles leaving the surface of the sample, where each of the measured energies corresponds to a different noble gas ion beam energy. The methods can include comparing at least some of the measured energies to energies measured for a reference sample to determine the dopant information.

The methods can include measuring a plurality of energies of the scattered noble gas particles and a plurality of angular directions of the scattered noble gas particles, where each of the energies corresponds to a different noble gas ion beam energy, and each of the angular directions corresponds to a different noble gas ion beam energy.

The methods can include determining information about masses of a plurality of different dopant particles in the sample based on the energies, the angular directions, or both. The methods can include determining a composition of two or more different dopant particles of the plurality of different dopant particles based on the information about the masses.

Embodiments can also include other features of the methods disclosed herein, as appropriate.

Embodiments can include one or more of the following advantages.

Relatively light gas ions such as helium ions can be used to form an ion beam that is used to determine dopant information for a sample of interest. In general, light atoms are less prone to implantation (e.g., becoming dopants themselves) in semiconductor substrate materials relative to certain heavier atoms. Using relatively light atoms can reduce damage to semiconductor substrates relative to heavier incident gas ions.

Exposure of samples to gas ion beams can be used to determine dopant information non-destructively, so that inspected substrates can still be used, and can be reintroduced into fabrication lines. This reduces scrap rates and enables a larger number of samples to be tested in a manufacturing environment.

Information about multiple dopants in a single sample can be obtained, including information about spatial distributions of the multiple dopants in a sample. If the sample is a semiconductor wafer, this information can be used as feedback to doping machines in a fabrication facility to refine manufacturing procedures.

Dopant information can be measured at high-resolution. As a result, the techniques disclosed herein can be applied to even the smallest existing semiconductor devices, which may be sensitive to even small variations in dopant concentration and/or location.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
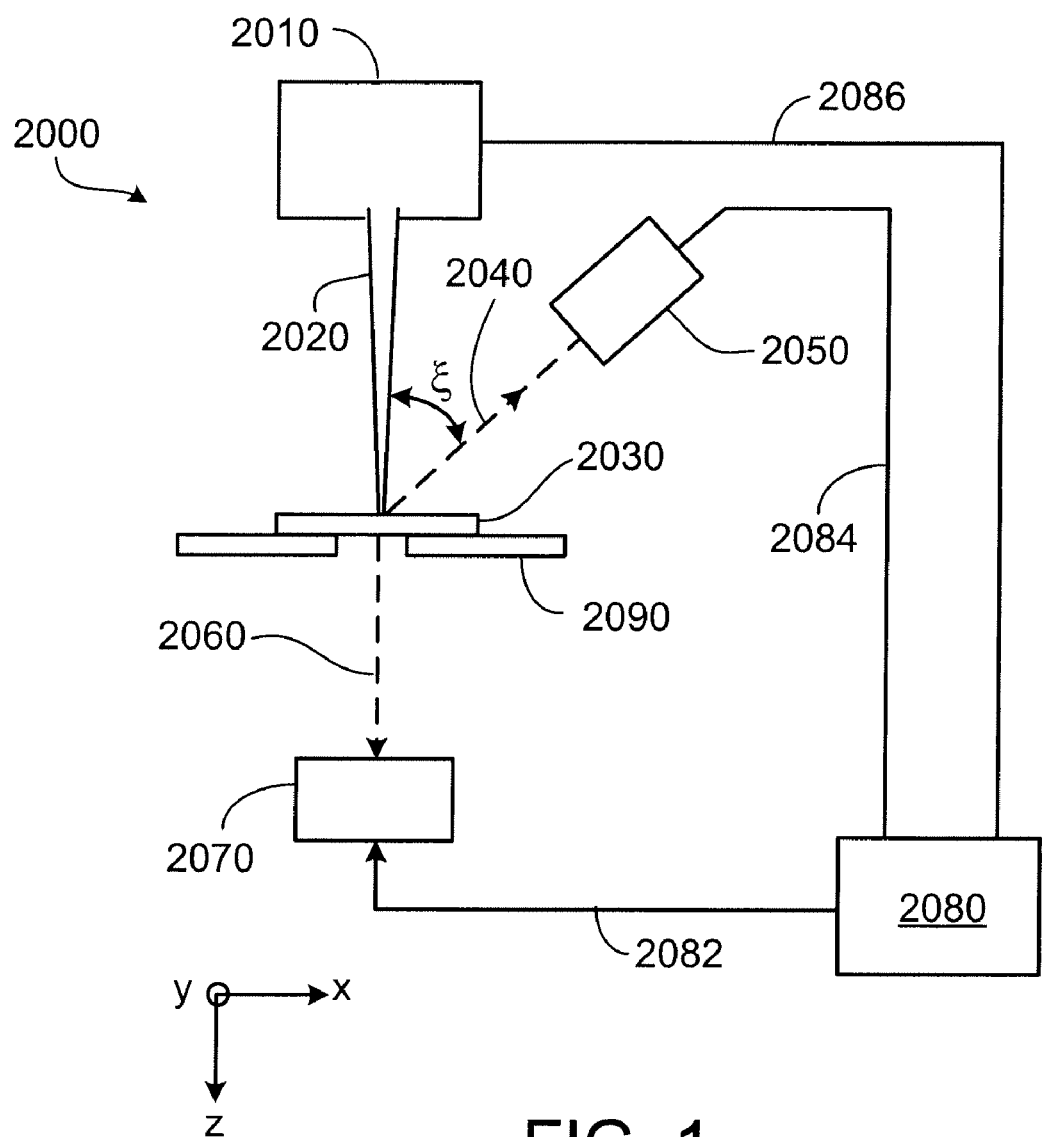
FIG. 1 is a schematic diagram of an embodiment of a dopant information measurement system.

Dopant metrology is a challenging and important task in a variety of fields such as semiconductor manufacturing and metal parts fabrication and analysis. Dopants typically include atoms and/or molecules that are introduced into a substrate material. Dopants can be introduced intentionally to control one or more properties of the substrate, for example. Alternatively, or in addition, certain dopants can be introduced into the substrate unintentionally as a result of the substrate's interaction with its environment. A variety of processes can be used to introduce dopants into a substrate; these include, but are not limited to: exposure of the substrate to an atomic or molecular beam that includes the dopants; exposure of the substrate to one or more chemical precursors that react to deposit dopants; and exposure of the substrate to gases or liquids that include dopants. In general, dopants can be introduced into a substrate as the substrate is fabricated, or after substrate fabrication is complete.

Disclosed herein are systems and methods for determining dopant information in samples. Samples can include semiconductor substrate materials formed of silicon, for example, although samples that include any substrate material can generally be interrogated by the systems and methods disclosed herein. Similarly, common dopants for semiconductor substrate materials include boron, phosphorus, and arsenic, although generally, any dopant can be interrogated. Dopants can also include molecular species such as methane, oxygen, oxides, fluorocarbons, binary semiconductor compounds, ternary semiconductor compounds, and other molecular species. Typically, for example, dopants are present within the sample at concentrations of about $2 \times 10^{18}$ cm$^{-3}$, although higher dopant concentrations (e.g., from $2 \times 10^{18}$ cm$^{-3}$ to $1 \times 10^{21}$ cm$^{-3}$) and lower dopant concentrations (e.g., from $1 \times 10^{16}$ cm$^{-3}$ to $2 \times 10^{18}$ cm$^{-3}$) are also typical.

The systems and methods disclosed herein use gas ion beams for measurements of dopant information. Typically, the gas ion beams are formed of helium ions, although other gas ions can also be used. Additional examples of gas ions that can be used to form the ion beams disclosed herein include hydrogen ions, neon ions, argon ions, krypton ions, and xenon ions. To determine dopant information, a gas ion beam is directed to be incident on a sample that includes dopants, and particles that leave the sample in response to the incident gas ion beam are measured.

This disclosure is divided into three main sections. In the first section, systems and methods for measurement of dopant information using a gas ion beam are disclosed. In the second section, applications that include measurement of dopant information are disclosed. In the third section, systems and methods for producing the gas ion beams used in the first section, and various detection systems and methods for particles leaving the sample, are disclosed.

I. Measurement of Dopant Information

A schematic diagram of a dopant information measurement system 2000 is shown in FIG. 1. System 2000 includes an ion beam source 2010, detectors 2050 and 2070, a sample stage 2090, and an electronic control system 2080. In some embodiments, for example, system 2000 can be an ion microscope system (or a portion thereof).

Ion beam source 2010 generates a gas ion beam 2020 that is focused by source 2010 onto sample 2030, which is positioned on stage 2090. Detector 2050 is generally positioned with respect to sample 2030 to detect particles 2040 that leave sample 2030 from the surface upon which gas ion beam 2020 is incident. Detector 2070 is generally positioned with respect to sample 2030 to detect particles 2060 that leave sample 2030 from the surface opposite the surface upon which gas ion beam 2020 is incident. Each of detectors 2050 and 2070 can be translated along each of the x-, y-, and z-directions, and can be rotated about each of x-, y-, and z-axes to enable detection of particles with a range of trajectories. System 2000 can also include further detectors in addition to detectors 2050 and 2070.

Detectors 2050 and 2070 can generally be configured to detect a variety of particles leaving sample 2030. In some embodiments, detector 2050 and/or detector 2070 can be configured to detect secondary electrons leaving sample 2030. The secondary electrons are produced from interactions between incident ions and the atoms of sample 2030 (e.g., atoms that form the substrate or the dopants). A secondary electron, as referred to herein, is an electron that is emitted from a sample and that has an energy of less that 50 eV. In general, secondary electrons are emitted from the sample surface at a range of angles and energies. However, the information of most interest is usually the total abundance of secondary electrons (as opposed to energy-resolved secondary electron information, or angle-resolved secondary electron information) because, as explained below, the total abundance of the secondary electrons is what can provide dopant information.

Secondary electrons can be detected using one or more appropriate detectors capable of detecting electrons (see discussion below regarding types of detectors). If multiple detectors are used, the detectors may all be the same type of detector, or different types of detectors may be used, and may generally be configured as desired. The detectors can be configured to detect secondary electrons leaving a surface of the sample, including the surface on which the ion beam impinges, the surface on the opposite side from where the ion beam impinges, or both.

Detected secondary electron signals can be used to form an image of a sample. Generally, the ion beam is raster-scanned over a field of view on the surface of the sample, and the secondary electron signal at each raster step (which corresponds to an individual pixel in an image) is measured by one or more detectors. Usually, each detector remains in fixed position relative to the sample as the ion beam is raster-scanned over the field of view of the surface of the sample. In certain embodiments, however, one or more detectors can be moved relative to the sample. For example, if a single detector is being used, moving the detector relative to the sample can yield angle-dependent information about the sample.

In some embodiments, detecting the total abundance of secondary electrons can yield material constituent information (e.g., elemental information, chemical environment information) about a sample. In general, each element or material in a given chemical environment will have a particular inherent secondary electron yield. As a result, the secondary electron total abundance at a given location on a surface generally depends on the material present at that location. Therefore, the change in the total abundance of secondary electrons as a function of the location of the ion beam on the surface of the sample, can be correlated to a change in the element(s) and/or material(s) present in the sample, providing material constituent information about the sample. In certain embodiments, specific materials in a sample can be identified based on quantitative measurements of secondary electron yields from the sample. For example, materials such as Al, Si, Ti, Fe, Ni, Pt, and Au have known secondary electron yields when exposed to a He ion beam under controlled conditions. An ion microscope (e.g., a gas field ion microscope) can be calibrated based on known secondary electron yields for various materials to identify the presence and relative abundance of a variety of different materials in a sample under study. For example, secondary electron yields for various materials are shown in Table I. The yields were measured at normal incidence of a He ion beam, and at an average ion energy of 21 keV. At non-normal angles of incidence, for example, the yields shown in Table I are typically scaled by a multiplicative factor that corresponds to the secant of the angle of incidence of the ion beam on the surface of the sample.

TABLE I

| Material | Z | M (amu) | Yield of secondary electrons |
| --- | --- | --- | --- |
| Aluminum | 13 | 27.0 | 4.31 |
| Silicon | 14 | 28.1 | 2.38 |
| Titanium | 22 | 47.9 | 3.65 |
| Iron | 26 | 55.8 | 3.55 |
| Nickel | 28 | 58.7 | 4.14 |
| Copper | 29 | 63.4 | 3.23 |
| Indium | 49 | 114.8 | 4.69 |
| Tungsten | 74 | 183.8 | 2.69 |
| Rhenium | 75 | 186.2 | 2.61 |
| Platinum | 78 | 195.1 | 7.85 |
| Gold | 79 | 197.0 | 4.17 |
| Lead | 82 | 207.2 | 4.57 |

In some embodiments, detecting the total abundance of secondary electrons can provide crystalline information about a sample. The total abundance of secondary electrons can vary depending on whether the ion beam is aligned with the crystal structure of the sample (e.g., aligned parallel to one of the unit vectors describing the crystal lattice) or not. If the ion beam is aligned with the crystal structure of the sample, the probability that ions in the ion beam can generally penetrate into a given distance into the sample without undergoing a collision with a sample atom (commonly referred to as channeling) is relatively high, resulting in a lower total abundance of secondary electrons. If, on the other hand, the ion beam is not aligned with the crystal structure, then the ions in the ion beam will have a lower probability of penetrating into the sample the given distance without undergoing a collision with a sample atom, resulting in a higher total abundance of secondary electrons. Therefore, the change in the total abundance of secondary electrons as a function of the ion beam location at the sample surface can be correlated to the crystalline information of the material at that location. For example, there may be regions of the sample surface where the secondary electron total abundance is substantially the same. Such regions can, for example, have the same crystal orientation, and the size of the regions can provide grain size and/or crystal size information (e.g., in a polycrystalline sample that includes multiple, oriented crystal domains), and/or can provide information regarding strained regions of sample (whether amorphous or crystalline) because the magnitude of the secondary electron total abundance for a material of a given chemical composition (e.g., elemental composition, material composition) can depend on the strain of the material.

Secondary electron imaging techniques can be applied to a variety of different classes of samples. An example of such a class of materials is semiconductor articles, such as patterned wafers, which can include, for example, multiple electrical conductors surrounded by a matrix of insulating material. Generally, secondary electron imaging techniques can be used for a wide range of ion beam testing applications of semiconductor articles.

Imaging samples using secondary electrons generated by exposure to an ion beam can provide a number of advantages relative to secondary electron imaging via other techniques, such as SEM. For example, the spot size of the ion beam on the sample can be smaller than the spot size of an electron beam from a SEM. As a result of the smaller spot size, the region of the sample that is exposed to the ion beam is more carefully controlled than the exposed region in a SEM.

Further, in general, because ions are heavier than electrons, scattering events do not disperse ions as readily within the sample as electrons are dispersed by scattering. As a result, He ions incident on the surface of a sample can interact with the sample in a smaller interaction volume than electrons in a SEM. Accordingly, secondary electrons detected in a gas field ion microscope (e.g., an ion microscope) can arise from a smaller region than the region giving rise to secondary electrons in a SEM with a similar spot size. Consequently, the secondary electrons which are generated by the ion beam can correspond to a more localized interrogation of the surface of the sample (e.g., with less lateral averaging of material properties) than the secondary electrons generated in a SEM.

In addition, the ion source also provides a greater depth of focus than an electron source. As a result, images of a sample obtained using an ion microscope (e.g., a gas field ion microscope) can show a larger portion of the sample—measured along the direction perpendicular to the sample surface—in focus than comparable images obtained from secondary electrons in a SEM.

Ion beams can also provide a more sensitive contrast mechanism for secondary electron images of a sample due to a larger range of secondary electron yields for different materials available when causing the secondary electrons to leave the sample due to the interaction of the ion beam with the sample, as compared to when causing the secondary electrons to leave the surface due to the interaction of an electron beam with the sample. Typically, for example, secondary electron yields for common materials such as semiconductors and metals vary from 0.5 to 2.5 for an incident electron beam. However, secondary electron yields for the same materials exposed to an ion beam can vary from 0.5 to 8. Thus, identification of different materials from secondary electron images can be performed more accurately using a gas field ion microscope (e.g., a He ion microscope) than in comparable SEM systems.

In certain embodiments, detector 2050 and/or detector 2070 can be configured to detect scattered particles that leave sample 2030. Some ions that are incident upon sample 2030 can be scattered from the sample and measured, and dopant information can be derived from the measurements. Incident ions that are scattered can remain ions, and can be detected as scattered ions. Alternatively, or in addition, incident ions that are scattered can combine with one or more electrons (e.g., a scattered He ion can combine with a single electron from the sample) and leave the sample as scattered neutral atoms. As referred to herein, a scattered ion is generated when an ion from the ion beam (e.g., a He ion) interacts with the sample and is scattered from the sample while remaining an ion (e.g., a He ion). A scattered neutral atom is generated when an ion from the ion beam (e.g., a He ion) interacts with the sample and is scattered from the sample, combining with one or more electrons during the interaction with the sample to form a neutral atom (e.g., a neutral He atom).

In certain embodiments, the detection of scattered particles can be used to determine material constituent information about the sample. One such approach involves measuring the total abundance of scattered particles. The total abundance of scattered particles can be detected using a single detector (e.g., a hemispherical detector) configured to detect scattered particles leaving a sample (e.g., the surface on which the ion beam impinges), or multiple detectors (e.g., located at different solid angles with respect to the surface of the sample and configured to detect scattered particles leaving the sample, for example, from the surface on which the ion beam is incident, at a range of angles and energies). In general, when shielding of Coulombic repulsion forces between incident ions and sample particles (e.g., dopant particles) by inner-shell electrons is relatively ineffective and can be neglected (e.g., at relatively high incident ion energies such as incident ion energies greater than about 100 keV), and/or when shielding of Coulombic repulsion forces is not negligible but can be accounted for, the scattering probability of an incident ion (and therefore the total abundance of scattered particles, assuming no effects from other factors such as surface topographical changes in the sample) is approximately proportional to the square of the atomic number (Z value) of the sample particle from which the ion scatters. Thus, as an example, when trying to distinguish copper (atomic number 29) from silicon (atomic number 14) in a semiconductor article, the total abundance of scattered particles from a copper atom at a surface of the semiconductor article will be approximately four times the total abundance of scattered particles from a silicon atom at the surface of the semiconductor article. As another example, when trying to distinguish tungsten (atomic number 74) from silicon (atomic number 14) in a semiconductor article, the total abundance of scattered particles from a tungsten atom at a surface of the semiconductor article will be approximately 25 times the total abundance of scattered particles from a silicon atom at the surface of the semiconductor article. As a further example, when trying to distinguish gold (atomic number 79) from silicon (atomic number 14) in a semiconductor article, the total abundance of scattered particles from a gold atom at a surface of the semiconductor article will be approximately 25 times the total abundance of scattered particles from a silicon atom at the surface of the semiconductor article. As an additional example, when trying to distinguish indium (atomic number 49) from silicon (atomic number 14) in a semiconductor article, the total abundance of scattered particles from an indium atom at a surface of the semiconductor article will be approximately 10 times the total abundance of scattered particles from a silicon atom at the surface of the semiconductor article.

Another approach to determining material constituent information about the sample by detecting scattered particles (which may be used in combination with, or instead of, total abundance detection) involves measuring scattered particles in an energy-resolved and angle-resolved fashion. For example, a detector can be used, for which the angle and energy of each detected scattered particle is known for each angle within the acceptance angle of the detector. By measuring the energy and scattering angle of the scattered particle, the mass of the sample particle (e.g., atom) that scattered the particle can be calculated based on the following relationship:

$$K\left(\frac{M}{M_a}, \theta_s\right) = \left[\frac{\sqrt{1 - \left(\frac{M}{M_a} \cdot \sin(\theta_s)\right)^2} + \left(\frac{M}{M_a}\right) \cdot \cos(\theta_s)}{\left(1 + \frac{M}{M_a}\right)^2}\right]^2 \quad (1)$$

where K is a kinematic factor for the scattered particle, M is the mass of the incident ion, $\theta_s$ is the scattering angle of the scattered particle, and $M_a$ is the mass of the sample particle that scatters the incident ion. The quantity K is related to the energy of the incident ion, $E_i$, and the energy of the scattered particle, $E_s$, according to:

$$K = \frac{E_s}{E_i} \quad (2)$$

Detectors configured to detect scattered particles (e.g., scattered ions and/or scattered neutral atoms) can, for example, be energy-resolving phosphor-based detectors, energy-resolving scintillator-based detectors, solid state detectors, energy-resolving electrostatic prism-based detectors, electrostatic spectrometers, energy-resolving Everhart-Thornley detectors, energy-resolving microchannel detectors, time-of-flight detectors, and/or magnetic spectrometers. In general, it is desirable for the detector to have a substantial acceptance angle. In some embodiments, the detector is stationary (e.g., an annular detector). In certain embodiments, the detector can sweep through a range of solid angles. Although a system for detecting energy-resolved and angle-resolved scattered particles that includes a single detector has been described, such a system can contain multiple (e.g., two, three, four, five, six, seven, eight) detectors. Often, the use of multiple detectors is desirable because it can allow for a larger acceptance angle of detected scattered particles.

In some embodiments, detecting the total abundance of scattered particles can provide crystalline information about a sample. The total abundance of scattered particles can vary depending on whether the ion beam is aligned with the crystal structure of the sample or not. If the ion beam is aligned with the crystal structure of the sample, the probability that ions in the ion beam can generally penetrate into a given distance into the sample without undergoing a collision with a sample atom (commonly referred to as channeling) is relatively high, resulting in a lower total abundance of scattered particles. If, on the other hand, the ion beam is not aligned with the crystal structure, then the ions in the ion beam will have a lower probability of penetrating into the sample the given distance without undergoing a collision with a sample atom, resulting in a higher total abundance of scattered particles. Therefore, the change in the total abundance of scattered particles as a function of the ion beam location at the sample surface can be correlated to the crystalline information about the material at that location. For example, there may be regions of the sample surface where the scattered particles' total abundance is substantially the same. Such regions can, for example, have the same crystal orientation, and the size of the regions can provide grain size and/or crystal size information (e.g., in a polycrystalline sample that includes multiple, oriented crystal domains), and/or can provide information regarding strained regions of sample (whether amorphous or crystalline) because the magnitude of the scattered particles' total abundance for a material of a given chemical composition (e.g., elemental composition, material composition) can depend on the strain of the material.

Alternatively or additionally, crystalline information about the surface of a sample can be obtained by exposing a region of the surface to an ion beam (without rastering the ion beam) and then measuring a pattern of the scattered particles (e.g., similar to a Kikuchi pattern obtained due to backscattered electrons from a sample surface exposed to an electron beam). The pattern of the scattered particles can be analyzed to determine, for example, the orientation, lattice spacing, and/or crystal type (e.g., body centered cubic, face centered cubic) of the material at the location of the sample surface that is exposed to the ion beam.

In general, scattered particles (e.g., scattered ions and/or scattered neutral atoms) are not formed when a sample surface is exposed to an electron beam of the type used in conventional SEMs, and thus none of the crystalline information or material constituent information obtainable via detected scattered particles is available with such SEMs. This is a significant advantage of a gas field ion microscope (e.g., a He ion microscope) as described herein relative to a conventional SEM.

Measurement of scattered He particles (e.g., scattered He ions and/or scattered neutral He atoms) using a gas field ion microscope (e.g., a He ion microscope) as described herein can offer a number of advantages relative to conventional Rutherford backscattering measurement devices. The spot size to which the incident ions can be focused at the surface of the sample can be significantly smaller than the spot size of conventional Rutherford backscattering measurement devices (typical spot sizes of 100 µm to 1 mm or more), allowing for the material constituent information about the sample to be more precisely localized than with conventional Rutherford backscattering measurement devices. Further, a gas field ion microscope (e.g., a He ion microscope) as described herein allows for pixel-by-pixel rastering across the sample surface, whereas Rutherford backscattering measurement devices do not have this capability. This can reduce the cost and/or complexity associated with determining material constituent information about the sample surface at various locations of the surface.

Detectors 2050 and/or 2070 shown in FIG. 1 can generally be configured to measure a variety of properties of particles leaving sample 2030. In some embodiments, detectors 2050 and/or 2070 can be configured to measure energies of particles leaving sample 2030. Suitable detectors for performing particle energy measurements are discussed below. In certain embodiments, detectors 2050 and/or 2070 can be configured to measure directions of particles leaving sample 2030 (e.g., angle-resolved detection of particles). Particle directions can be measured, for example, by positioning detectors 2050 and/or 2070 at a plurality of selected angles ξ with respect to a central axis of ion beam 2020, and detecting particles at each of the angles. This technique permits measurement of particle flux as a function of detection angle, for example.

Ion beam source 2010 includes a variety of components configured to produce ion beam 2020. The components, configuration, and modes of operation of ion beam source 2010 will be discussed in further detail below.

Typically, ion beam 2020 is formed by noble gas atoms. For example, ion beam 2020 can be formed by helium ions, and scattered particles measured by detectors 2050 and/or 2070 include helium ions and/or neutral helium atoms. In some embodiments, ion beam 2020 can be formed by other noble gas ions such as neon ions. In certain embodiments, ion beam 2020 can be formed by non-noble gas ions such as hydrogen ions.

Electronic control system 2080 regulates each of the components of system 2000 via electronic signals transmitted to and received from the components along communication lines 2082, 2084, and 2086. Electronic control system 2080 typically includes a processor, a display unit, and an input interface for receiving commands from a system operator. Following detection of particles by detectors 2050 and/or 2070, the detectors transmit electronic signals to control system 2080. The electronic signals are processed by control system 2080's processor to derive dopant information about sample 2030.

In some embodiments, information about dopants in the sample is obtained from one or more images of the sample that are obtained by system 2000. As discussed above, images of the sample can be obtained by detecting particles that leave the sample under the influence of an incident ion beam. Typically, to interrogate a particular sample, a region of interest on the sample (e.g., which can include the entire sample or a portion thereof) is first identified. Electronic control system 2080 separates the region of interest into a series of discrete regions that correspond to image pixels, and then directs ion beam source 2010 to sweep ion beam 2020 across the region of interest on sample 2030, pixel by pixel, in a raster pattern. At each pixel, sample 2030 is exposed to ion beam 2020 and particles leaving sample 2030 are measured by detectors 2050 and/or 2070. Detectors 2050 and/or 2070 transmit electronic signals to control system 2080 that correspond to each of the pixels in the region of interest on sample 2030. Various exposure parameters (e.g., dwell time, ion beam energy, ion beam flux, ion beam spot size, ion beam convergence half-angle, ion beam brightness, ion beam etendue) can be controlled by control system 2080 via control signals that are dispatched to ion beam source 2010.

In some embodiments, the electrical signals corresponding to individual pixels that are received by control system 2080 correspond to abundance measurements of particles by detectors 2050 and/or 2070. For example, detectors 2050 and/or 2070 can detect a total number of particles that have left sample 2030 over an elapsed measurement time as a total particle intensity. The total particle intensity for each pixel can be measured and the resulting values transmitted to control system 2080. Control system 2080 can assemble the pixel-by-pixel intensity measurements into images of sample 2030, where intensity values in the images correspond to a total abundance of particles that have left sample 2030 during exposure to ion beam 2020.

In certain embodiments, images of sample 2030 that are based on measured abundances of particles leaving sample 2030 can be obtained at more than one detector orientation. For example, two or more images of sample 2030 can be obtained, each at a different angle ξ with respect to a central axis of ion beam 2020. The multiple images can be analyzed to determine angle-resolved information about sample 2030.

Generally, dopant information that is obtained from one or more images of sample 2030 is derived from variations in image intensity, e.g., image contrast, due to dopants present in sample 2030. Without wishing to be bound by theory, it is believed that there are a number of dopant-related mechanisms that can lead to variations in image intensity.

A. Spatial Secondary Electron Yield Variations

Secondary electron yields are generally known (or can be determined) for a wide variety of substrate materials, as indicated in Table I. In the absence of other features that lead to image intensity variations, exposing sample 2030 (including only a substrate material and no dopants) to ion beam 2020 produces a relatively uniform image, with only small spatial variations in image intensity. However, dopants—which have different chemical compositions from the substrate material—have secondary electron yields that differ from the secondary electron yield of the substrate material. As a result, exposing a sample that includes a substrate and dopants to ion beam 2020 produces an image of the sample that includes intensity variations that are due to the dopants. The presence of the intensity variations provides qualitative identification of the presence of dopants. Analysis of the intensity variations can provide quantitative information about the dopants.

B. Secondary Electron Escape Probability

As discussed above, ion beam 2020 produces secondary electrons in sample 2030 when the sample is exposed to the ion beam. A fraction of the secondary electrons that are produced migrate to a surface of sample 2030 and escape the sample, where they can be collected and measured by detectors 2050 and/or 2070. For a uniform sample 2030 that includes only a substrate material and no dopants, the secondary electron escape probability (in the absence of other sample features that affect this property) is relatively uniform across the sample surface. As a result, images of sample 2030 have only small variations in spatial intensity that arise from variations in secondary electron escape probability.

However, dopants present in sample 2030 can alter the secondary electron escape probability from sample 2030. For example, the presence of dopants in sample 2030 will affect electron mobility, charge dissipation, and local electric fields within the sample and in regions that immediately surround the sample (e.g., in regions adjacent to sample surfaces). Changes in any of these properties can alter the local secondary electron escape probability in the vicinity of the dopants. As a result, secondary electron images of sample 2030 include spatial variations in intensity that are due to dopants present in the sample. Quantitative dopant information can be obtained by analyzing the intensity variations.

C. Secondary Electron Measurement Efficiency

When a sample is exposed to an ion beam, an induced voltage due to the incident ions is produced at the sample surface. Certain types of secondary electron detectors include a charged collection plate that is at a different electrical potential than the sample surface. The efficiency with which secondary electrons generated in the sample are measured by a detector of this type depends upon the potential difference between the sample surface and collection plate. Generally, higher potential differences lead to more efficient detection of secondary electrons.

For samples that include only a uniform substrate material and no dopants, a relatively spatially uniform potential difference is present between the sample surface and a collection plate of a detector. However, dopants in the sample can locally alter surface charging properties of the sample. In particular, dopants can affects rates at which surface charges are dissipated. As a result, exposure of samples that include dopants to ion beam 2020 can produce spatial variations in the potential difference between the sample surface an a detector collection plate. The potential difference variations yield intensity variations in secondary electron images of the sample. Quantitative dopant information can be obtained by analyzing the intensity variations.

D. Gas Ion Scattering Probability

A certain fraction of gas ions that are incident upon sample 2030 will scatter from the sample, and the scattered particles (e.g., ions and/or neutral atoms) can be measured by detectors 2050 and/or 2070. For samples that include only a uniform substrate material and no dopants, the ion scattering probability does not exhibit large spatial variations. As a result, images of the sample that are based upon scattered ions have relatively small spatial intensity variations.

Ion scattering probabilities depend upon the sample particles that scatter the incident ions. As a result, dopants in sample 2030 produce spatial variations the ion scattering probability. Images of sample 2030 that are based on scattered particles (e.g., ions and/or neutral atoms) include spatial intensity variations that indicate the presence of dopants. Quantitative dopant information can be obtained via analysis of the intensity variations.

Other dopant-related mechanisms can also produce intensity variations in images of sample 2030. For example, in some embodiments, incident gas ions that are scattered from sample 2030 can produce additional secondary electrons as they leave the sample (e.g., secondary electrons in addition to those produced from an initial collision with a sample atom). Secondary electron production in local regions of the sample will depend on the presence or absence of dopants in the regions.

As another example, dopants in sample 2030 can alter not only ion scattering probabilities, but also ion scattering angles. Changes to both can manifest as intensity variations in samples images that are based on scattered particles.

Figure 2:
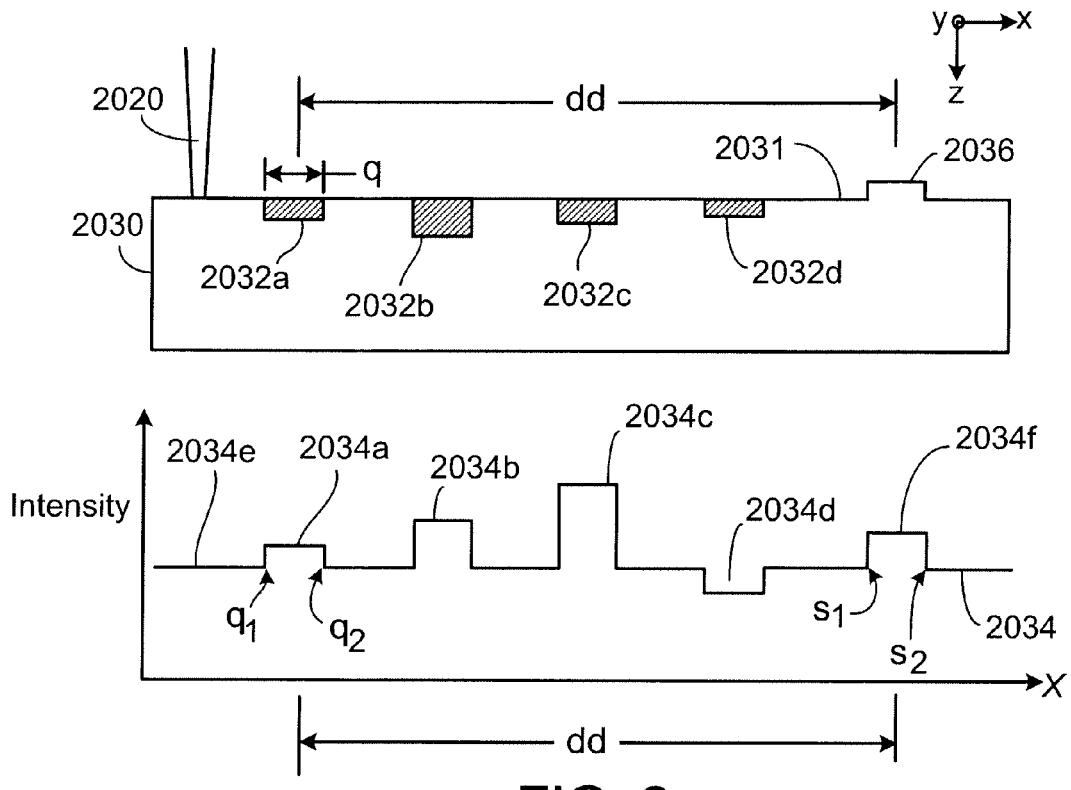
FIG. 2 is a schematic cross-sectional diagram of a sample that includes a plurality of doped regions, and a measured secondary electron abundance curve for the sample.

The systems and methods disclosed herein can be used to determine a variety of different types of dopant information, including concentrations of dopants in the sample, locations of dopants in the sample, masses of dopant particles in the sample, chemical composition of dopant particles in the sample, and other information. FIG. 2 shows a schematic cross-sectional diagram of a sample 2030 that includes four doped regions 2032*a-d*. Ion beam 2020 is rastered across surface 2031 of sample 2030 to measure secondary electrons that leave sample 2030 in response to the incident ions from beam 2020. Curve 2034 shows measured secondary electron abundance as a function of position for a line scan across sample 2030 in a direction parallel to the x-direction. From left to right along curve 2034, a first portion 2034*e* of curve 2034 is a baseline portion and corresponds to secondary electron generation from a substrate material of sample 2030. A second portion 2034*a* of curve 2034 corresponds to secondary electron emission from doped region 2032*a* of sample 2030. Dopants in region 2032*a* have a higher secondary electron yield than the substrate material. As a result, measured secondary electron abundance 2034*a* for region 2032*a* is larger than the baseline value for the substrate.

A third portion 2034*b* of secondary electron abundance curve 2034 corresponds to doped region 2032*b* of sample 2030. Doped region 2032*b* has a larger thickness, measured in a direction parallel to the z-direction, than doped region 2032*a*. As a result, the total secondary electron abundance from doped region 2032*b* is larger than the total secondary electron abundance from doped region 2032*a*, and so portion 2034*b* of curve 2034 has a larger intensity than portion 2034*a*.

A fourth portion 2034*c* of curve 2034 corresponds to doped region 2032*c*. Doped region 2032*c* is thinner in the z-direction than doped region 2032*b*. However, dopant concentration in region 2032*c* is significantly larger than in region 2032*b*. As a result, the total secondary electron abundance from region 2032*c* is larger than from region 2032*b*, and so portion 2034*c* of curve 2034 has a larger intensity than portion 2034*b*.

A fifth portion 2034*d* of curve 2034 corresponds to doped region 2032*d*. Region 2032*d* includes a dopant that is different from the dopant in regions 2032*a-c*. The dopant in region 2032*d* has a lower secondary electron yield than the substrate material of sample 2030. As a result, the intensity of portion 2034*d* of curve 2034 is lower than the intensities of portions 2034*a-c*, and also lower than portion 2034*e* which corresponds to the undoped substrate material.

Using the information provided by curve 2034, the presence of dopants in sample 2030 can be identified. Further, the locations of the dopants can be determined. For example, in the one-dimensional cross-section shown in FIG. 2, the edges of doped region 2032*a* can be determined from curve 2034 as points $q_1$ and $q_2$. Various algorithms can be used to locate the edge positions $q_1$ and $q_2$ based on curve 2034. For example, in some embodiments, edge positions can be selected as a midpoint between local maximum and a local minimum intensities in the vicinity of the edges. With reference to curve 2034, the edge positions $q_1$ and $q_2$ can be identified as the points having intensities that are half-way between the intensities of portions 2034*e* and 2034*a*.

In some embodiments, one or more dimensions such as maximum dimensions of doped regions can be determined. For example, doped region 2032*a* has a maximum dimension q, as shown in FIG. 2. The maximum dimension q can be obtained from curve 2034 as the difference between edge positions $q_1$ and $q_2$. In general, edge positions of doped regions can be determined in three dimensions for sample 2030 and accordingly, dimensions—including maximum dimensions—of the doped regions can also be determined in three dimensions.

Figure 3:
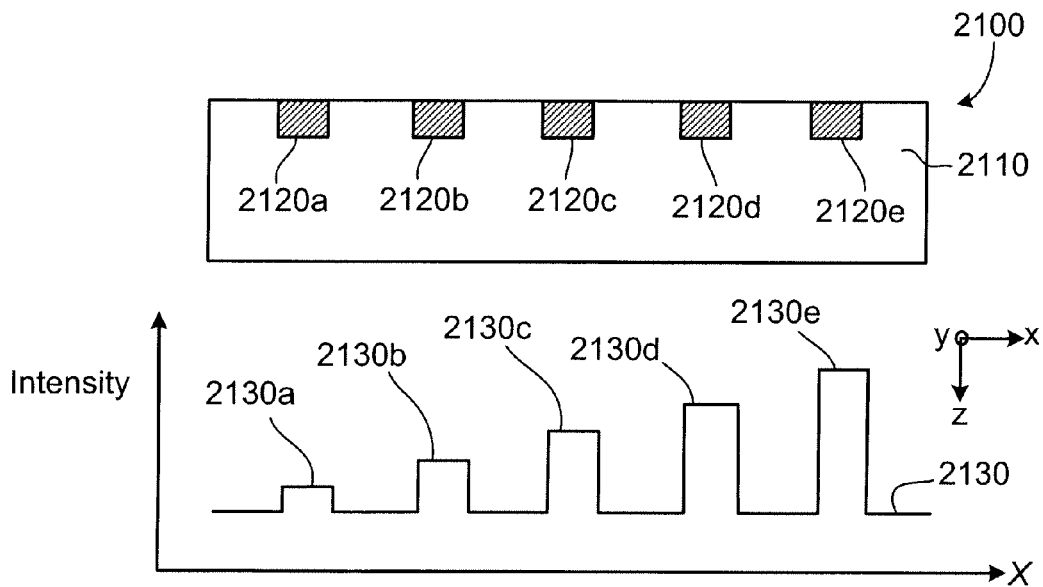
FIG. 3 is a schematic cross-sectional diagram of a standard sample.

In certain embodiments, quantitative information can be obtained about concentrations of dopants in sample 2030. One method for obtaining quantitative dopant concentration information includes comparing values of measured total abundance of secondary electrons for doped regions of sample 2030 to total abundances of secondary electrons measured from a standard sample. In general, the standard sample is formed from the same substrate material as sample 2030, and includes a plurality of regions, each of which includes a known dopant at a known concentration. The measured total abundances of secondary electrons for each of the regions are compared to measured abundances for sample 2030, and dopant concentrations in sample 2030 can be quantitatively determined. An embodiment of a standard sample 2100 is shown in FIG. 3 in a cross-sectional view. Standard sample 2100 includes a substrate material 2110 and a plurality of doped regions 2120*a-e*. The measured total abundance of secondary electrons from standard sample 2100 when exposed to ion beam 2020 is shown as curve 2130. Each of doped regions 2120*a-e* features dopant concentrations that increase progressively, and in the increasing concentrations are reflected in the increasing intensities of portions 2130*a-e* of curve 2130. The intensities of portions 2130*a-e* can be interpolated to match measured secondary electron abundances for regions of sample 2030 to obtain quantitative dopant concentration information.

In some embodiments, the positions of doped regions can be correlated (e.g., registered) with one or more reference marks on a sample. For example, sample 2030 in FIG. 2 includes a reference mark 2036 that corresponds to a portion 2034*f* of total secondary electron abundance curve 2034. The edges of reference mark 2036 can first be located by determining positions $s_1$ and $s_2$ from curve 2034. Then, a midpoint of reference mark 2036 can be determined as the mid-point of $s_1$ and $s_2$. A distance dd between doped region 2032*a* and reference mark 2036 can then be determined based on curve 2034. Using methods and systems disclosed herein, any of the doped regions in sample 2030 can be registered with respect to reference mark 2036.

The preceding discussion of FIGS. 2 and 3 relates to measuring abundances of secondary electrons that are generated in sample 2030 in response to exposure to ion beam 2020. However, it should be recognized that analogous dopant information can be derived from measurements of scattered particles (e.g., scattered ions and/or scattered neutral atoms) from sample 2030. In particular, measurements of abundances of scattered particles from different regions of sample 2030 can be used to identify the presence of dopants, to determine locations of dopants and of edges of doped regions, and to determine dimensions (e.g., maximum dimensions) of doped regions.

In some embodiments, energy- and angle-resolved measurements of scattered particles from sample 2030 can also be used to determine masses of dopant particles. As discussed above in connection with Equations (1) and (2), the masses of dopant particles can be determined if incident ion and scattered particle energies, and scattering angles, are known. As a result, the systems and methods disclosed herein can be used to identify masses of dopant particles (e.g., dopant atoms, and dopant molecules or fragments thereof).

In certain embodiments, dopant composition information can be obtained from the masses of dopant particles. For example, in certain embodiments, dopants are known to be atomic (e.g., dopant particles include only single atoms). Determination of the mass of such dopant particles therefore uniquely identifies the atoms. In some circumstances, dopant particles can be polyatomic. However, if the range of possible dopants is relatively small, determination of dopant particle masses can still be used to identify the composition of polyatomic dopant particles due to the relatively small number of possible dopant particle compositions.

Figure 4:
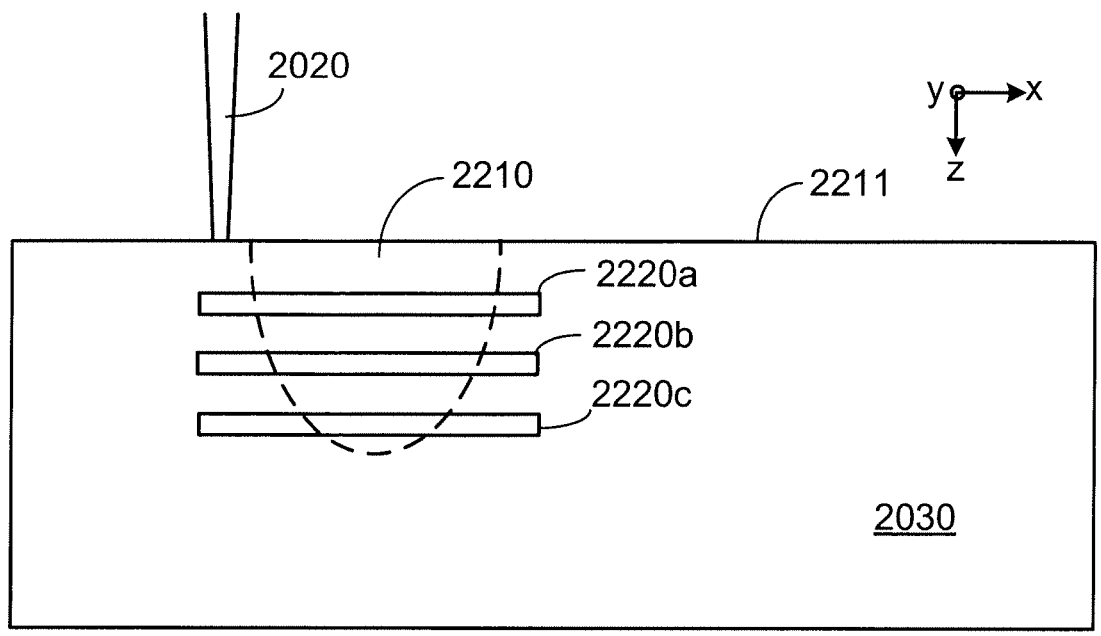
FIG. 4 is a schematic cross-sectional diagram that shows measurement of depth-dependent dopant information in a sample.

Information about dopant location and concentration at one or more depths below a surface of sample 2030 can also be determined. In general, by varying the ion beam energy of ion beam 2020, the penetration depth of incident ions into sample 2030 (e.g., the depth below surface 2031, measured in a direction parallel to the z-direction and normal to a surface of the sample) can be controlled. In some embodiments, dopant locations and concentrations at selected depths can be determined by obtaining a plurality of images at different ion beam incident energies. FIG. 4 shows a schematic cross-sectional diagram of a sample 2030 that includes a doped region 2210 upon which ion beam 2020 is incident. Images of sample 2030 are obtained by measuring secondary electrons from sample 2030. A first image of sample 2030 is obtained with an incident energy of ion beam 2020 controlled such that scattering of incident ions and secondary electron generation occurs mainly within region 2220*a*. A second image of sample 2030 is obtained with a higher incident ion beam energy, so that scattering and secondary electron generation occurs mainly within region 2220*b*. A third image of sample 2030 is obtained with a still-higher incident ion beam energy, so that scattering and secondary electron generation occurs mainly within region 2220*c*. Data from the three images can be combined to reveal features of the doped region such as the location and shape in three dimensions of region 2210. Further, comparison of measured signal intensities in the images can provide information about dopant concentrations in the three regions, and can permit determination of variations in dopant concentration as a function of depth below surface 2211 of sample 2210 (e.g., measured in a direction parallel to the z-direction). In the example shown in FIG. 4, three images of sample 2030 are obtained. In general, however, any number of images can be obtained for different incident ion energies; a larger number of images can be obtained to achieve improved resolution and accuracy, for example.

Selection of suitable ion beam energies can also be used to obtain mass and composition information about dopants at different depths below a surface of the sample. For example, energies and angular directions of scattered particles can be measured for different incident ion beam energies. As discussed above, the energy- and angle-resolved scattered particle measurements can be used to identify dopant particle masses, and therefrom, to determine dopant particle compositions. Different ion beam energies can be used to selectively obtain this information for regions at selected depths below the sample surface. This enables measurement and identification of specific dopants at different positions within the sample, and also enables determination of changes in overall dopant composition (e.g., when two or more different dopants exist) as a function of below-surface depth. The masses and compositions of each of the two or more different dopants can be determined via the systems and methods disclosed herein.

By adjusting the incident ion energy to a particular average value, incident ions in ion beam 2020 can be restricted so that incident ion scattering and secondary electron generation substantially occurs only from surface atoms of the sample (e.g., atoms within 5 nm of a surface of sample). Using this configuration, dopant location and quantitative dopant concentration information at the surface of the sample can be determined, with relatively small contributions from dopants that are positioned deeper within the sample.

Figure 5:
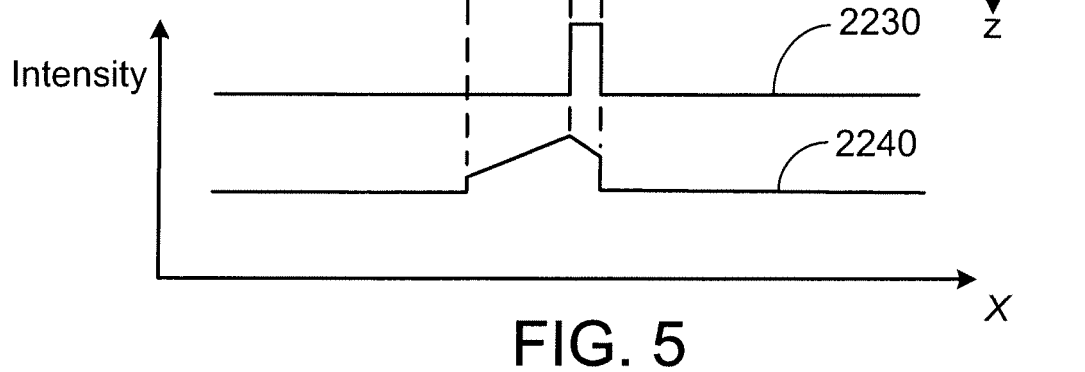
FIG. 5 is a schematic cross-sectional diagram that shows measurement of depth-dependent dopant information in a sample using a tilted ion beam.

In certain embodiments, dopant location and concentration information can be determined by measuring one or more images of the sample with a central axis of the incident ion beam tilted at a non-zero angle with respect to a sample surface normal. FIG. 5 shows a schematic cross-sectional diagram of a sample 2030 that includes a doped region 2210. A central axis 2021 of ion beam 2020 is oriented at an angle κ with respect to a normal to surface 2031 of sample 2030. Curves 2230 and 2240 show measured scattered ion abundances for two different orientations of ion beam 2020. Curve 2230 corresponds to an angle κ=0—that is, ion beam 2020 is normally incident upon sample 2030. The shape of curve 2230 is similar to the shape of curve 2034 in FIG. 2.

Curve 2240 corresponds to a non-zero angle of incidence of ion beam 2020—that is, the angle κ>0. Due to angle of beam 2020, doped region 2210 appears to be wider than it actually is in curve 2240. By analyzing the shape of curve 2240, and with knowledge of κ, dopant information such as dopant location and concentration (including concentration variations) as a function of depth below surface 2031 can be determined.

Figure 6:
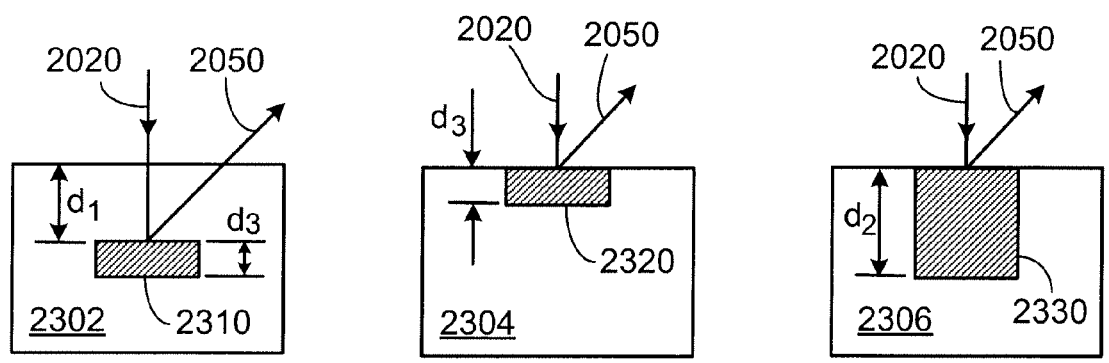
FIG. 6 is a schematic cross-sectional diagram showing three samples with different doped regions and measured energy distributions for each.
Figure 6:
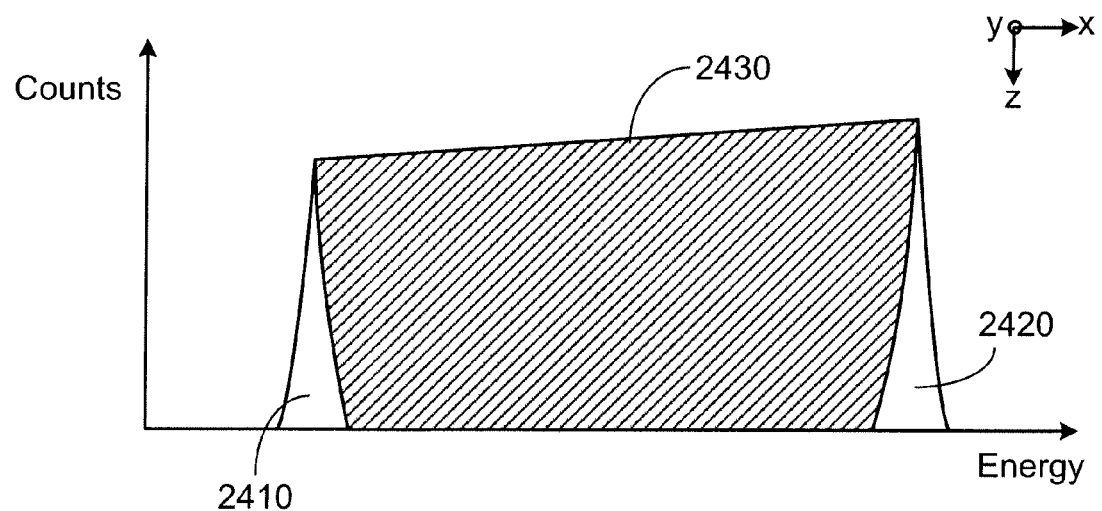

In some embodiments, dopant location and concentration information can be determined based on energy measurements of scattered particles (e.g., ions and/or neutral atoms). FIG. 6 shows schematic cross-sectional diagrams of three samples 2302, 2304, and 2306, each of which includes a doped region (2310, 2320, and 2330, respectively). Information about dopant locations and concentrations can be determined by measuring energies of scattered particles from each sample. Sample 2302 includes a doped region 2310 of thickness $d_3$ and positioned at a distance $d_1$, both measured in a direction parallel to the z-direction. Dopant-scattered particles 2050 from sample 2310 have energies that fall within an energy distribution given by curve 2410. The distribution is relatively narrow due to the relatively small thickness of region 2310. The peak of the distribution is at relatively low energy because incident ions penetrate sample 2310 relatively deeply, and therefore lose a significant amount of energy during scattering.

In contrast, sample 2304 includes a doped region 2320 of thickness $d_3$ measured in a direction parallel to the z-direction, and positioned at a surface of sample 2304. Dopant-scattered particles 2050 have energies that fall within an energy distribution given by curve 2420. The distribution is relatively narrow due to the relatively small thickness of region 2320, but the peak of the distribution is at relatively high energy because incident ions do not penetrate sample 2304 very deeply before scattering.

Sample 2330 includes a doped region 2330 of thickness $d_2$ measured in a direction parallel to the z-direction. Thickness $d_2$ is significantly larger than thickness $d_3$. As a result, dopant-scattered particles exhibit a wider energy distribution, because scattering can occur anywhere within doped region 2330. The dopant-scattered particles 2050 have energies that fall within an energy distribution given by curve 2430 (the shaded area between curves 2410 and 2420). This distribution is relatively wide due to the thickness $d_2$ of doped region 2330.

Dopant-scattered particles can be separated from other scattered particles by filtering the scattered particle flux based on the particle energies. The filtering can be accomplished by a physical device such as a deflector, or electronically by disregarding certain portions of the measured energy distribution of scattered particles. By analyzing the energies of particles scattered from dopants in a sample of interest, both dopant location and concentration information can be determined for the sample. For example, by determining an average scattered particle energy, information about the depth of a doped region below a surface of the sample can be obtained. Further, by determining a width and shape of the energy distribution, a thickness and shape of the doped region can be calculated. Comparing the integrated area under the energy distribution curve to energy distribution data measured for standard samples, quantitative concentration information for doped regions can be obtained.

Figure 7:
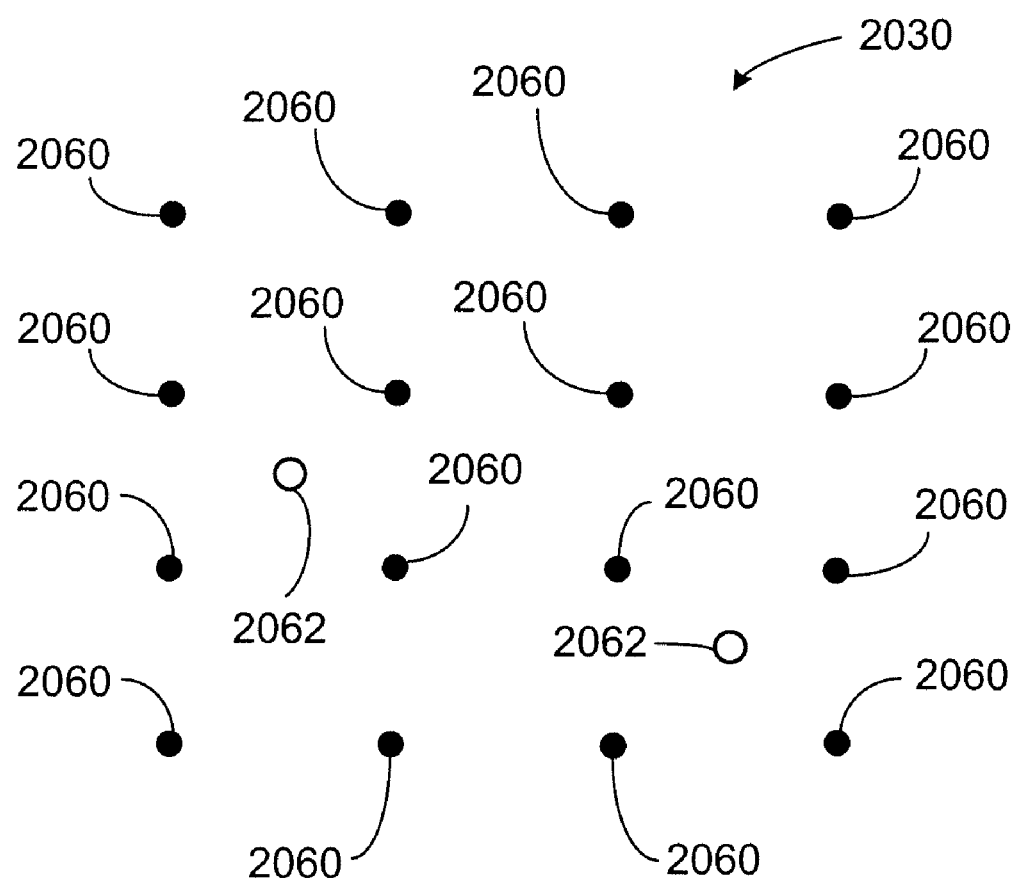
FIG. 7 is a schematic diagram of a sample that includes dopant atoms.

In certain embodiments, dopant particles that occupy interstitial sites within a sample crystal structure can be identified. As discussed above, images of crystalline samples (e.g., secondary electron images) typically exhibit ion channeling effects. When incident ions are directed along crystal channels in the sample, the incident ions penetrate more deeply, on average, into the crystal structure than ions that are not incident along channel structures. As a result, fewer secondary electrons from these incident ions reach the surface of the sample and are detected, and the crystal channels appear darker in sample images than the surrounding sample structures. However, if dopant particles are present in interstitial sites (e.g., within the crystal channels), scattering of incident ions occurs from the dopant particles, and the dopant particles therefore appear as bright regions in sample images. FIG. 7 shows a schematic diagram of a sample 2030 that is formed from a substrate material that includes atoms 2060. Two dopant particles 2062 are positioned in locations that correspond to channels between atoms 2060. From the presence of bright regions in regions of sample images that correspond to the crystal channels in sample 2030, dopant particles 2062 that are positioned in interstitial sites can be identified.

In certain embodiments, both secondary electrons and scattered particles (e.g., scattered ions and/or scattered neutral atoms) can be measured to determine dopant information for a sample. For example, in certain embodiments, images based on measured secondary electrons can be used to determine location and quantitative concentration information about dopant particles, and energy- and angle-resolved measurements of scattered particles can be used to measure masses of dopant particles and to determine the composition of the dopant particles based on the masses. In general, combinations of any of the particle measurements disclosed herein can be used to determine dopant information about samples. In some embodiments, images of the sample that are obtained from secondary electron measurements and scattered particle measurements can be combined to assist in determining dopant information.

Depending upon the nature of a particular sample and its dopants, it may be possible in certain circumstances to distinguish, at least in part, between various physical mechanisms that lead to image contrast when dopants are present in a sample. For example, in some embodiments, different ion beam currents can be used to isolate the effects of surface charging on secondary electron images of doped samples. When the ion beam current is increased, for example, the number of secondary electrons produced increases in linear proportion to the ion beam current. However, a larger ion beam current deposits a relatively larger amount of surface charge on a surface of the sample. If the surface charge cannot be dissipated rapidly, the increased surface charge reduces the escape probability of secondary electrons from the sample, counteracting the effect of the larger number of secondary electrons produced. Multiple images of the sample, each corresponding to a different incident ion beam current, can be obtained and analyzed to determine whether dopants increase or decrease the escape probability of electrons from a sample of interest, and to obtain other dopant information of the type disclosed herein.

Certain secondary electron detectors include a collector plate (e.g., a particle selector) that is maintained at a particular voltage with respect to the sample of interest to collect secondary electrons that leave the sample. The efficiency with which secondary electrons generated in the sample are measured by a detector of this type depends upon the potential difference between the sample surface and collection plate. By obtaining two or more images of a sample at different sample-plate potential energy differences, the effects on secondary electron detection efficiency due to the presence of dopants in the sample can be determined, along with other dopant information of the type disclosed herein.

In some embodiments, surface charging of the sample—which may lead to reduced contrast in secondary electron images of doped samples—can be mitigated by exposing the sample to electron beam, e.g., a beam from an electron flood gun. In general, when ions are incident on a surface of a sample, secondary electrons are produced and leave the sample, resulting in the surface having a net positive charge. Excess positive charges on the surface of the sample can produce a number of undesirable effects. For example, in certain embodiments, positive charging of the surface of the sample can limit the ability of detectors to detect secondary electrons that leave the sample due to the interaction of the ion beam with the sample. Attractive forces between positive charges at the surface of the sample and the secondary electrons can decelerate the electrons, preventing the electrons from reaching a detector.

In some embodiments, positive charging of the surface of the sample can cause inaccurate ion beam rastering. Deflection and deceleration of the incident ion beam as a result of the electric field created by positive charges at the surface of the sample can reduce the energy of the incident ions, and change their trajectories in difficult-to-predict fashion.

If the net positive charge on the surface of the sample becomes large enough, the surface of the sample can act as an electrostatic mirror for incident ions, deflecting ions away from the surface of the sample before the ions reach the surface of the sample.

Figure 8:
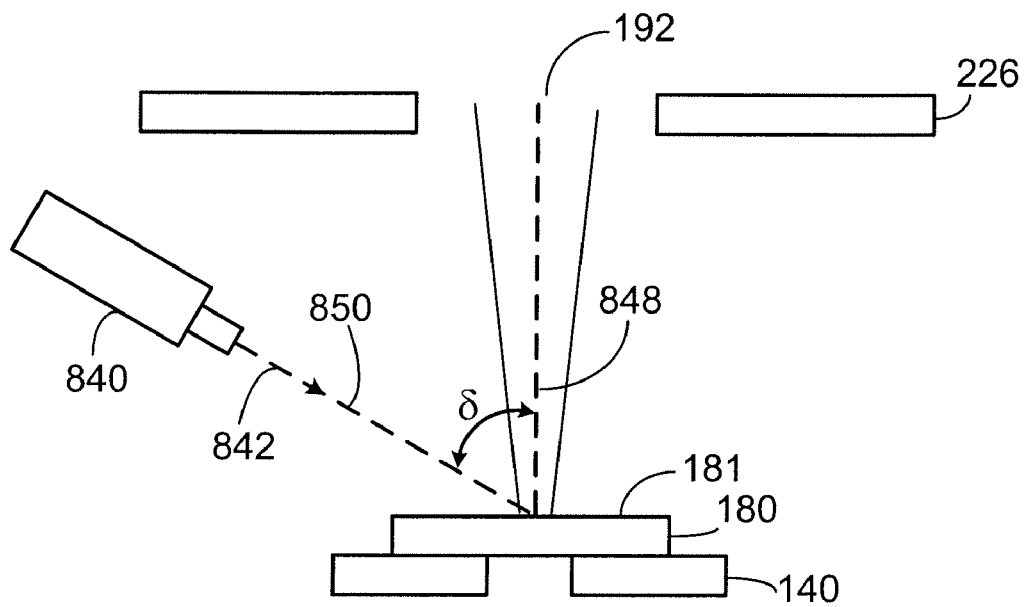
FIG. 8 is a schematic diagram of a portion of a gas field ion microscope including a flood gun.

A flood gun capable of delivering a flux of electrons to the surface of the sample can be used to counteract surface charging effects. FIG. 8 shows a portion of a gas field ion microscope that includes a flood gun 840 configured to deliver an electron beam 842 to surface 181 of sample 180 while a He ion beam 192 is incident on surface 181. The electron flux on surface 181 can, in general, be controlled so that surface charging effects are counterbalanced by electron beam 842 to the extent desired.

Figure 9:
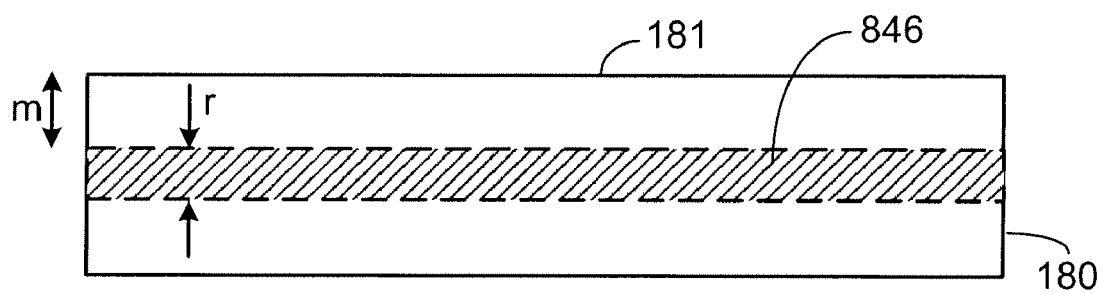
FIG. 9 is a schematic diagram of a sample including a sub-surface charge layer.

While FIG. 8 depicts ion beam 192 and electron beam 842 simultaneously impinging on surface 181 of sample 180, other approaches may be used. For example, prior to exposing surface 181 to ion beam 192, flood gun 840 can be configured to deliver electron beam 842 to sample 180 to create a charge layer 846 in a sub-surface region of sample 180 (FIG. 9). Layer 846 has an average depth m below surface 181, and layer 846 has a thickness r measured in a direction normal to surface 181. Generally, the depth m and thickness r, as well as the density of electrons in layer 846, can be controlled by the energy of the electrons in electron beam 842, the angle of incidence of the electrons in electron beam 842 with respect to surface 181, and the total dosage of electrons delivered to sample 180.

In some embodiments, when incident on surface 181, the average energy of the electrons in electron beam 842 is adjustable. For example, the average energy of the electrons can be 500 eV or more (e.g., 1 keV or more, 2 keV or more), and/or 20 keV or less (e.g., 15 keV or less, 10 keV or less). For example, when incident on surface 181, the average energy of the electrons in electron beam 842 can be from 500 eV to 20 keV (e.g., from 1 keV to 15 keV, from 2 keV to 10 keV).

The angle of incidence $\delta$ of the electrons in electron beam 842 with respect to surface 181 corresponds to the angle between a principal trajectory 850 of electron beam 842 and a normal 848 to surface 181. In general, $\delta$ is 0° or more (e.g., 10° or more, 20° or more), and/or 80° or less (e.g., 70° or less, 60° or less). For example, $\delta$ can be from 0° to 70° (e.g., from 0° to 10°, from 40° to 60°).

In certain embodiments, the total current of electrons delivered to sample 180 is 10 pA or more (e.g., 100 pA or more, 1 nA or more, 10 nA or more), and/or 100 µA or less (e.g., 10 µA or less, 1 µA or less, 500 nA or less, 100 nA or less). For example, the total current of electrons delivered to sample 180 can be from 10 pA to 1 µA (e.g., from 100 pA to 100 nA, from 1 nA to 10 nA).

In some embodiments, m is 10 nm or more (e.g., 25 nm or more, 50 nm or more, 75 nm or more, 100 nm or more), and/or 500 nm or less (e.g., 400 nm or less, 300 nm or less, 200 nm). For example, m can be from 10 nm to 500 nm (e.g., from 25 nm to 500 nm, from 50 nm to 500 nm, from 75 nm to 400 nm, from 100 nm to 400 nm).

In certain embodiments, multiple flood guns can be used. For example, in some embodiments, different flood guns can be used to expose different portions of surface 181 of sample 180 to electrons. In certain embodiments, each flood gun can be used to expose the same portion of surface 181 to electrons. Optionally, different flood guns can be operated at different times. For example, one or more flood guns can be used to expose surface 181 to electrons before surface 181 is exposed to incident ions (e.g., to form a sub-surface charge layer), while one or more different flood guns can be used to expose surface 181 to electrons while surface 181 is also being exposed to incident ions. In some embodiments, all the flood guns can be used to expose surface 181 to electrons before surface 181 is exposed to incident ions (e.g., to form a sub-surface charge layer), whereas in certain embodiments, all the flood guns can be used to expose surface 181 to electrons while surface 181 is also being exposed to incident ions. Other combinations may also be used.

II. Applications

The methods and systems disclosed herein can be used for a number of applications. Foremost among these are applications in semiconductor manufacturing and metrology. Semiconductor manufacturing errors that result in overdoped or underdoped wafers are both costly to correct and time-consuming to diagnose. As chip feature sizes continue to be reduced, accurate, high-resolution measurements of dopant information will be important to reduce failure rates. For example, transistors can include contacts that sample wafer regions of less than 100 atoms. If doped wafer regions are sampled, even small doping errors can lead to malfunctioning of the transistors due to the relatively small number of atoms that bridge the chip and the transistor. Accordingly, high-resolution, non-destructive dopant measurements will be critical to achieving continued miniaturization.

In some embodiments, ion microscopes (e.g., gas field ion microscopes) can include appropriate componentry to allow the microscopes to be used in-line for the analysis of samples, such as samples relevant to the semiconductor industry (e.g., wafer samples). In certain embodiments, for example, ion microscopes may be automated with a high-speed loadlock for standard sized semiconductor wafers. In some embodiments, the systems may include a wafer stage capable of putting a portion of a sample wafer under the ion microscope at high speed. The ion microscope may also include a scan system capable of high-speed rastering of metrology patterns. Optionally, the ion microscope may also include a charge neutralization scheme to reduce sample charging. The ion microscope may also include a wafer height control module for adjusting working distances. In certain embodiments, the system may be configured so that individual dies (e.g., having lengths on the order of 50 mm) can be imaged.

Another application is in the field of failure testing and analysis of metal parts. Ion microscopes can be used to identify and examine metal corrosion in various devices and materials. For example, metal fixtures and devices used in nuclear power plants, military applications, and biomedical applications can undergo corrosion due to the harsh environments in which they are deployed. Ion microscopes can be used to construct images of these and other devices based on the relative abundance of hydrogen in the devices, which serves as reliable indicator of corrosion. In effect, hydrogen atoms are present as dopants in these materials, and both location and concentration information can be determined for the hydrogen atoms. This information can be used to assess structural integrities and failure probabilities for the devices.

A further application includes dopant metrology of exposed subsurface features of a sample. In some applications, subsurface features of a sample can be exposed by using a gas ion beam to remove overlying portions of the sample. A noble gas ion beam, such as a helium ion beam, can be used to etch (e.g., sputter away) portions of the sample to expose subsurface regions of the sample. Alternatively, or in addition, another gas ion beam such as a gallium ion beam can be used to etch the sample prior to determining dopant information with a noble gas ion beam. In some embodiments, dopant metrology systems can include both a noble gas ion source such as a helium ion source, and another gas ion source such as a gallium ion source, where the noble gas ion source is configured to determine dopant information for exposed portions of the sample, and the other gas ion source is configured to expose selected portions of the sample by removing overlying portions of the sample.

In some applications, removal of selected portions of the sample exposes a cross-section of the sample, which can then be interrogated with the noble gas ion beam to determine dopant information about the sample. The dopant information can include dopant location, concentration, mass, composition, and other information as a function of position within the sample. In certain applications, removal of selected portions of the sample by a gas ion beam can be used to form a thin lamella sample. Thin lamella samples can be interrogated with noble gas ion beams either in reflection mode or transmission mode; that is, particles that leave the sample and are detected to determine dopant information about the sample can leave from a surface of the sample where the noble gas ion beam is incident, or from a surface opposite the surface where the noble gas ion beam is incident.

III. Ion Beam Systems

This section discloses systems and methods for producing ion beams, and detecting particles that leave a sample of interest due to exposure of the sample to an ion beam. The systems and methods can be used to determine dopant information including dopant location, concentration, particle mass, particle composition, and other information. Typically, the gas ion beams that are used to interrogate samples are produced in multipurpose microscope systems.

Microscope systems that use a gas field ion source to generate ions that can be used in sample analysis (e.g., imaging) are referred to as gas field ion microscopes. A gas field ion source is a device that includes an electrically conductive tip (typically having an apex with 10 or fewer atoms) that can be used to ionize neutral gas species to generate ions (e.g., in the form of an ion beam) by bringing the neutral gas species into the vicinity of the electrically conductive tip (e.g., within a distance of about four to five angstroms) while applying a high positive potential (e.g., one kV or more relative to the extractor (see discussion below)) to the apex of the electrically conductive tip.

Figure 10:
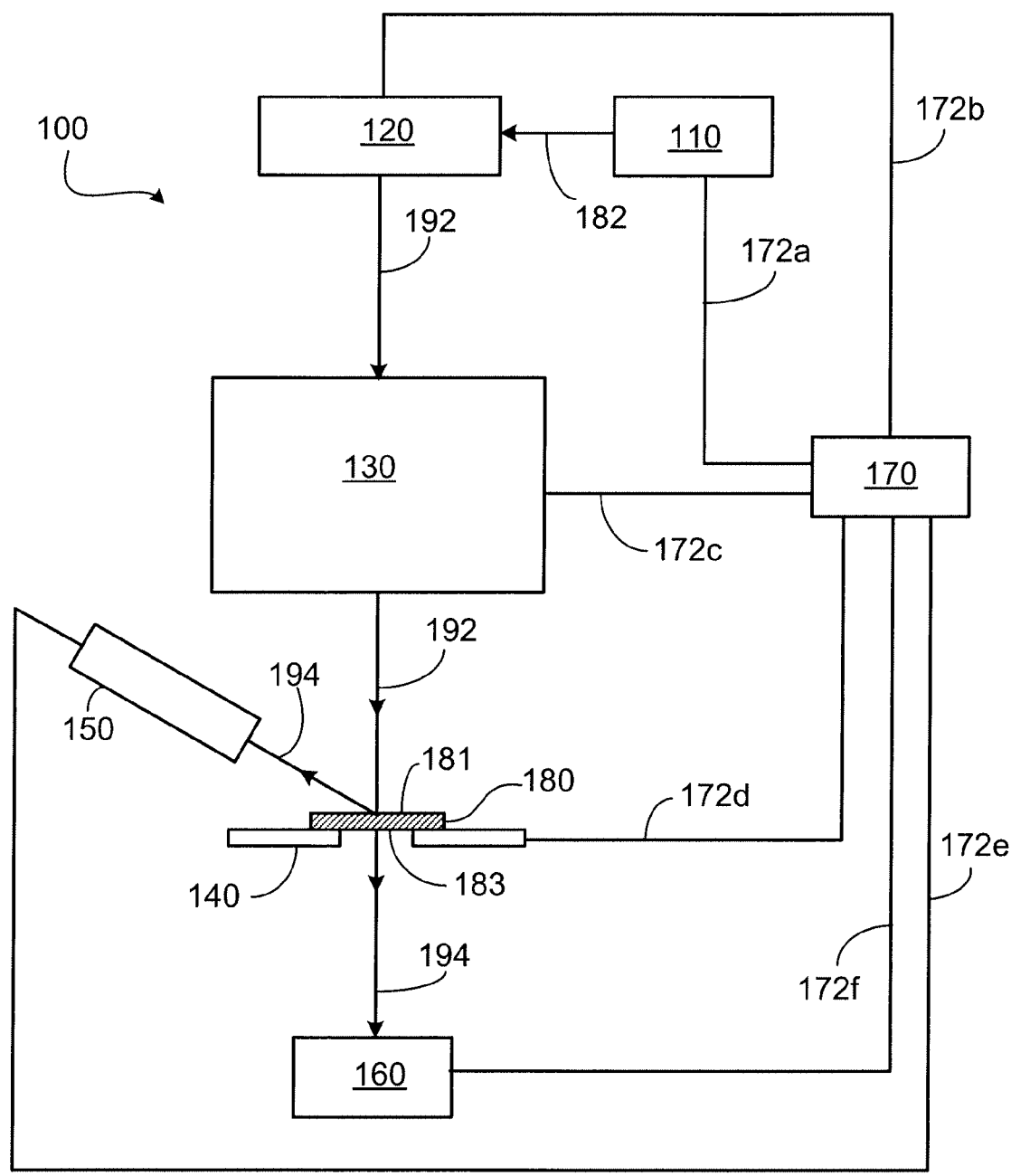
FIG. 10 is a schematic diagram of an ion microscope system.

FIG. 10 shows a schematic diagram of a gas field ion microscope system 100 that includes a gas source 110, a gas field ion source 120, ion optics 130, a sample manipulator 140, a front-side detector 150, a back-side detector 160, and an electronic control system 170 (e.g., an electronic processor, such as a computer) electrically connected to various components of system 100 via communication lines 172a-172f. A sample 180 is positioned in/on sample manipulator 140 between ion optics 130 and detectors 150, 160. During use, an ion beam 192 is directed through ion optics 130 to a surface 181 of sample 180, and particles 194 resulting from the interaction of ion beam 192 with sample 180 are measured by detectors 150 and/or 160.

In general, it is desirable to reduce the presence of certain undesirable chemical species in system 100 by evacuating the system. Typically, different components of system 100 are maintained at different background pressures. For example, gas field ion source 120 can be maintained at a pressure of approximately $10^{-10}$ Torr. When gas is introduced into gas field ion source 120, the background pressure rises to approximately $10^{-5}$ Torr. Ion optics 130 are maintained at a background pressure of approximately $10^{-8}$ Torr prior to the introduction of gas into gas field ion source 120. When gas is introduced, the background pressure in ion optics 130 typically increase to approximately $10^{-7}$ Torr. Sample 180 is positioned within a chamber that is typically maintained at a background pressure of approximately $10^{-6}$ Torr. This pressure does not vary significantly due to the presence or absence of gas in gas field ion source 120.

Figure 11:
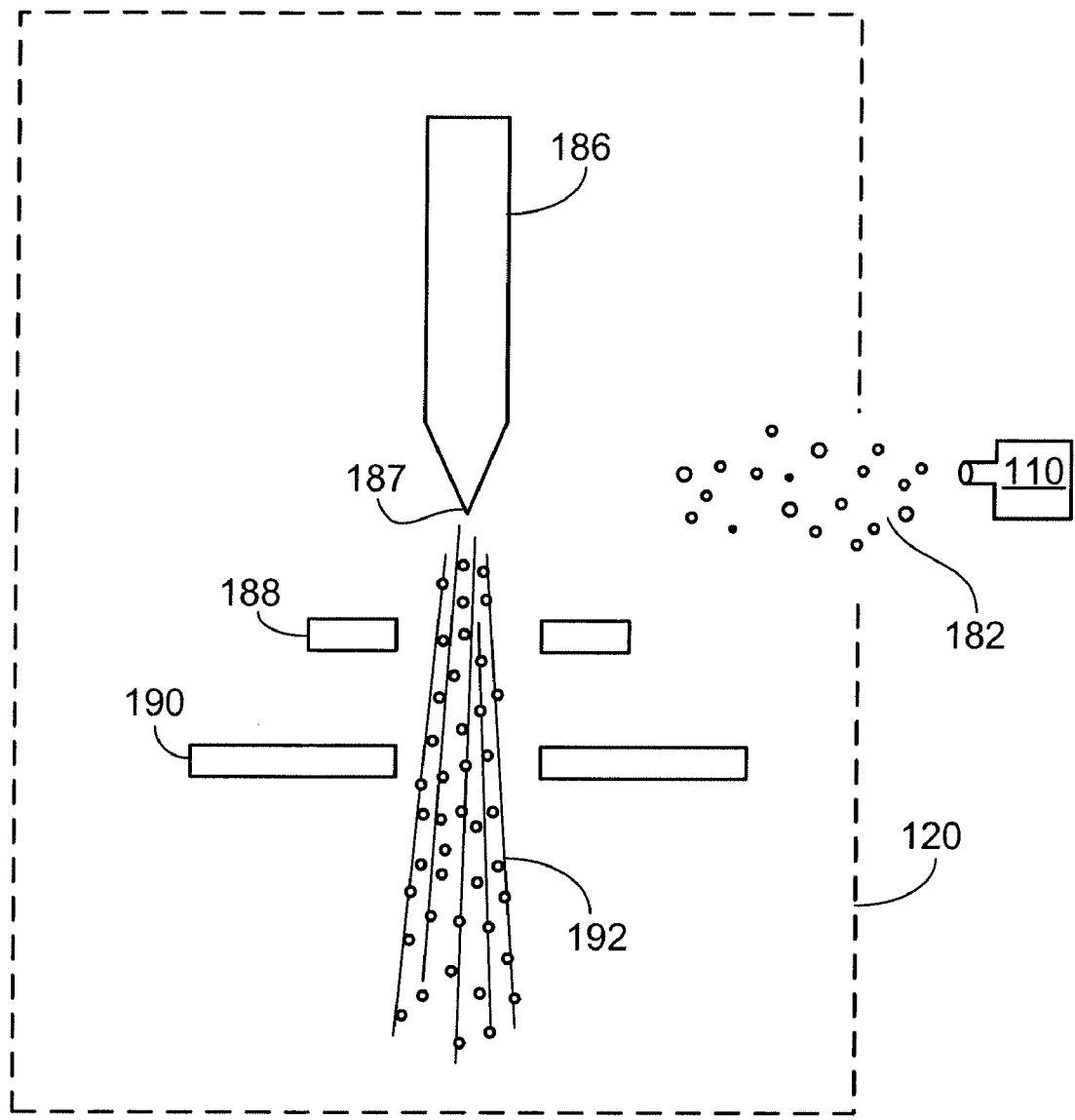
FIG. 11 is a schematic diagram of a gas field ion source.

As shown in FIG. 11, gas source 110 is configured to supply one or more gases 182 to gas field ion source 120. As described in more detail below, gas source 110 can be configured to supply the gas(es) at a variety of purities, flow rates, pressures, and temperatures. In general, at least one of the gases supplied by gas source 110 is a noble gas (helium (He), neon (Ne), argon (Ar), krypton (Kr), xenon (Xe)), and ions of the noble gas are desirably the primary constituent in ion beam 192. In general, as measured at surface 181 of sample 180, the current of ions in ion beam 192 increases monotonically as the pressure of the noble gas in system 100 increases. In certain embodiments, this relationship can be described by a power law where, for a certain range of noble gas pressures, the current increases generally in proportion to gas pressure. During operation, the pressure of the noble gas is typically $10^{-2}$ Torr or less (e.g., $10^{-3}$ Torr or less, $10^{-4}$ Torr or less), and/or $10^{-7}$ Torr or more (e.g., $10^{-6}$ Torr or more, $10^{-5}$ Torr or more) adjacent the tip apex (see discussion below). In general, it is desirable to use relatively high purity gases (e.g., to reduce the presence of undesirable chemical species in the system). As an example, when He is used, the He can be at least 99.99% pure (e.g., 99.995% pure, 99.999% pure, 99.9995% pure, 99.9999% pure). Similarly, when other noble gases are used (Ne gas, Ar gas, Kr gas, Xe gas), the purity of the gases is desirably high purity commercial grade.

Optionally, gas source 110 can supply one or more gases in addition to the noble gas(es). As discussed in more detail below, an example of such a gas is nitrogen. Typically, while the additional gas(es) can be present at levels above the level of impurities in the noble gas(es), the additional gas(es) still constitute minority components of the overall gas mixture introduced by gas source 110. As an example, in embodiments in which He gas and Ne gas are introduced by gas source 110 into gas field ion source 120, the overall gas mixture can include 20% or less (e.g., 15% or less, 12% or less) Ne, and/or 1% or more (e.g., 3% or more, 8% or more) Ne. For example, in embodiments in which He gas and Ne gas are introduced by gas source 110, the overall gas mixture can include from 5% to 15% (e.g., from 8% to 12%, from 9% to 11%) Ne. As another example, in embodiments in which He gas and nitrogen gas are introduced by gas source 110, the overall gas mixture can include 1% or less (e.g., 0.5% or less, 0.1% or less) nitrogen, and/or 0.01% or more (e.g., 0.05% or more) nitrogen. For example, in embodiments in which He gas and nitrogen gas are introduced by gas source 110, the overall gas mixture can include from 0.01% to 1% (e.g., from 0.05% to 0.5%, from 0.08 to 0.12%) nitrogen. In some embodiments, the additional gas(es) are mixed with the noble gas(es) before entering system 100 (e.g., via the use of a gas manifold that mixes the gases and then delivers the mixture into system 100 through a single inlet). In certain embodiments, the additional gas(es) are not mixed with the noble gas(es) before entering system 100 (e.g., a separate inlet is used for inputting each gas into system 100, but the separate inlets are sufficiently close that the gases become mixed before interacting with any of the elements in gas field ion source 120).

Gas field ion source 120 is configured to receive the one or more gases 182 from gas source 110 and to produce gas ions from gas(es) 182. Gas field ion source 120 includes an electrically conductive tip 186 with a tip apex 187, an extractor 190 and optionally a suppressor 188. Typically, the distance from tip apex 187 to surface 181 of sample 180 (not shown in FIG. 2) is five cm or more (e.g., 10 cm or more, 15 cm or more, 20 cm or more, 25 cm or more), and/or 100 cm or less (e.g., 80 cm or less, 60 cm or less, 50 cm or less). For example, in some embodiments, the distance from tip apex 187 to surface 181 of sample 180 is from five cm to 100 cm (e.g., from 25 cm to 75 cm, from 40 cm to 60 cm, from 45 cm to 55 cm).

Electrically conductive tip 186 can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, electrically conductive tip 186 can be formed of an alloy. In some embodiments, electrically conductive tip 186 can be formed of a different material (e.g., carbon (C)).

During use, tip 186 is biased positively (e.g., approximately 20 kV) with respect to extractor 190, extractor 190 is negatively or positively biased (e.g., from −20 kV to +50 kV) with respect to an external ground, and optional suppressor 188 is biased positively or negatively (e.g., from −5 kV to +5 kV) with respect to tip 186. Because tip 186 is formed of an electrically conductive material, the electric field of tip 186 at tip apex 187 points outward from the surface of tip apex 187. Due to the shape of tip 186, the electric field is strongest in the vicinity of tip apex 187. The strength of the electric field of tip 186 can be adjusted, for example, by changing the positive voltage applied to tip 186. With this configuration, un-ionized gas atoms 182 supplied by gas source 110 are ionized and become positively-charged ions in the vicinity of tip apex 187. The positively-charged ions are simultaneously repelled by positively charged tip 186 and attracted by negatively charged extractor 190 such that the positively-charged ions are directed from tip 186 into ion optics 130 as ion beam 192. Suppressor 188 assists in controlling the overall electric field between tip 186 and extractor 190 and, therefore, the trajectories of the positively-charged ions from tip 186 to ion optics 130. In general, the overall electric field between tip 186 and extractor 190 can be adjusted to control the rate at which positively-charged ions are produced at tip apex 187, and the efficiency with which the positively-charged ions are transported from tip 186 to ion optics 130.

As an example, without wishing to be bound by theory, it is believed that He ions can be produced as follows. Gas field ion source 120 is configured so that the electric field of tip 186 in the vicinity of tip apex 187 exceeds the ionization field of the un-ionized He gas atoms 182, and tip 186 is maintained at a relatively low temperature. When the un-ionized He gas atoms 182 are in close proximity to tip apex 187, the He atoms can be polarized by the electric field of the tip, producing a weakly attractive force between He atoms 182 and tip apex 187. As a result, He atoms 182 may contact tip apex 187 and remain bound (e.g., physisorbed) thereto for some time. In the vicinity of tip apex 187, the electric field is high enough to ionize He atoms 182 adsorbed onto tip apex 187, generating positively charged He ions (e.g., in the form of an ion beam).

Figure 12:
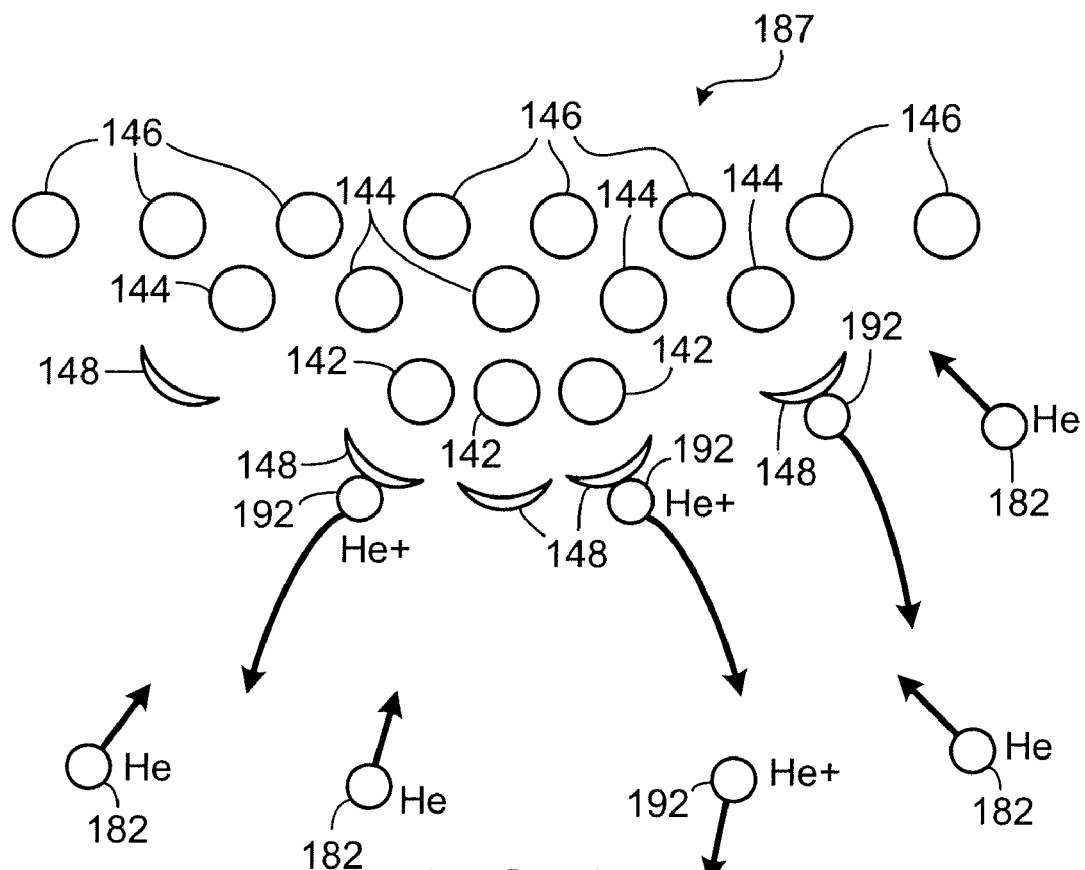
FIG. 12 is a schematic representation of an enlarged side view of an embodiment of a tip apex.

FIG. 12 is a schematic representation of tip apex 187 (formed of W(111), see discussion below). Tip apex 187 includes layers of atoms arranged to form atomic shelves. A terminal atomic shelf is formed by atoms 142. A second atomic shelf is formed by atoms 144, and a third atomic shelf is formed by atoms 146. Neutral gas atoms 182 delivered by gas source 110 are present in the vicinity of tip apex 187. Atoms 182 become polarized due to the electric field of tip apex 187, and experience a relatively weak attractive force that causes atoms 182 to move towards tip apex 187, as indicated by the arrows on atoms 182.

Depending upon the strength of the tip's electric field, each atoms in the atomic shelves near tip apex 187 can have a corresponding ionization disk 148. An ionization disk 148 is a region of space in which a neutral He atom, venturing thereinto, has a high probability of undergoing ionization. Typically, ionization of a neutral He atom occurs via electron tunneling from the neutral He atom to a tip apex atom. Ionization disks 148 therefore represent spatial regions in which He ions are generated, and from which the He ions emerge.

The sizes of the ionization disks 148 for particular tip apex atoms are dependent upon the shape of tip apex 187 and the electrical potential applied to tip apex 187. In general, ionization of He atoms can occur in spatial regions adjacent to tip apex 187 where the local electric field exceeds the ionization potential of He atoms. For a large electric potential applied to tip apex 187, therefore, many tip atoms will have ionization disks. In addition, the local electric field in the vicinity of tip apex 187 depends upon the shape of tip apex 187. For a relatively sharp tip apex, the local electric field in the vicinity of tip apex 187 will be relatively high. For a relatively blunt tip apex, the local electric field, even in the vicinity of tip apex 187, will be smaller.

Ionization disks 148 corresponding to individual atoms of tip apex 187 are spatially separated from one another in FIG. 12. In some embodiments, if the electric field of tip apex 187 is sufficiently large, ionization disks from more than one atom (e.g., atoms 142) can overlap spatially, creating a larger ionization disk that spans a region of space proximal to multiple tip apex atoms. By reducing the electric field at tip apex 187, the volume of space occupied by ionization disks 148 can be reduced, and the geometry depicted in FIG. 12 can be realized where a few tip apex atoms each have their own individual, spatially separated ionization disks. Because, in many instances, the shape of tip apex 187 is not easily altered during use of ion source 120, the electric field in the vicinity of tip apex 187 is typically controlled by adjusting the electrical potential applied to tip apex 187.

By further reducing the potential applied to tip apex 187, some of the ionization disks in FIG. 12 can be eliminated. For example, tip apex 187 is not as sharp in the vicinity of second atomic shelf atoms 144, and by reducing the potential applied to tip apex 187, the electric field of tip apex 187 in the vicinity of atoms 144 can be reduced so that He atom ionization does not occur with high probability in these regions. As a result, ionization disks corresponding to atoms 144 are no longer present. However, the electric field of tip apex 187 in the vicinity of terminal shelf atoms 142 can still be high enough to cause He atom ionization, and so ionization disks 148 corresponding to atoms 142 remain. By carefully controlling the electrical potential applied to tip apex 187, ion source 120 can operate so that the only ionization disks present correspond to terminal shelf atoms 142, and the ionization disks corresponding to the terminal shelf atoms are spatially separated from one another. As a result, a He atom that is ionized in the vicinity of tip apex 187 is produced via ionization in the vicinity of a particular terminal shelf atom.

Neutral He atoms 182 have a higher probability of undergoing ionization the longer they remain within ionization disks 148. The polarization of He atoms which is induced by the electric field of tip apex 187, and which causes polarized He atoms to move toward tip apex 187, further ensures that the polarized He atoms remain bound to tip apex 187, increasing the amount of time that the He atoms 182 remain within ionization disks 148, and increasing the probability of ionization of the polarized He atoms over time.

Polarized He atoms can also move from one position to another along the surface of tip apex 187. Because the attractive force between a polarized He atom and tip apex 187 depends on the local strength of the electric field of tip apex 187 at the position of the polarized He atom, the motion of polarized He atoms tends to transport the atoms toward the end of tip apex 187 of tip 186 (e.g., toward terminal shelf 142) where the local electric field is highest. This transport mechanism of polarized He atoms, in combination with control over the electrical potential applied to tip 186 (e.g., to ensure that discrete ionization disks corresponding to only terminal shelf atoms 142 are present), can be used to operate ion source 120 such that a He ion beam 192 is produced by gas field ionization source 120, where individual He ions in the ion beam are generated via the interaction of He gas with one of the terminal shelf atoms 142. Ion beam 192 therefore includes a plurality of He ions from each of the terminal shelf atoms 142, where each He ion can be attributed to ionization at one of the terminal shelf atoms 142.

As discussed above, in general, the size and shape of ionization disks 148 can be modified by changing the electrical potential applied to tip apex 187, and adjacent ionization disks 148 can be made to overlap with a suitably large applied potential, or maintained spatially distinct from one another by a suitably small applied potential. Typically, ionization disks 148 are spaced from tip atoms 142, 144, and 146 by a distance of approximately 0.4 nm. Individual ionization disks corresponding to tip atoms typically have a thickness of approximately 0.02 nm, measured in a direction along a line joining a given disk and its corresponding atom. Ionization disks 148 typically have a diameter, measured in a direction normal to the line joining a given disk and its corresponding atom, of approximately the diameter of the corresponding atom.

Figure 13:
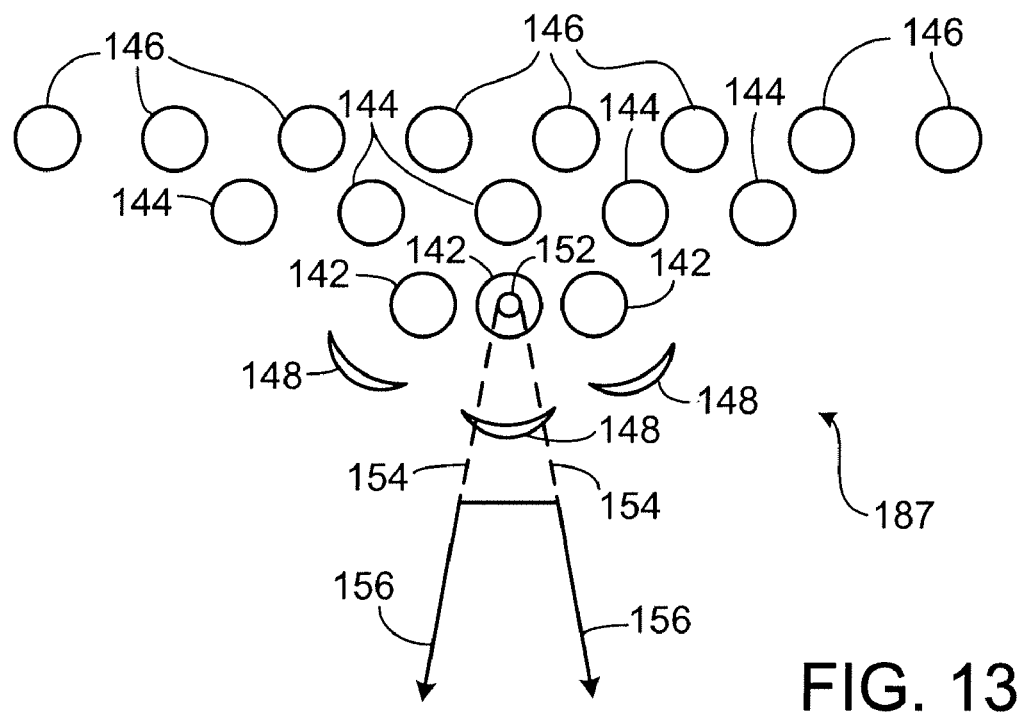
FIG. 13 is a schematic representation of an enlarged side view of the tip of FIG. 12.

FIG. 13 shows an operating configuration of tip apex 187 where the electrical potential applied to tip 186 produces three ionization disks 148, each of which corresponds to one of three terminal atomic shelf atoms 142. Once He ions are produced in the vicinity of tip apex 187, they are rapidly accelerated away from the tip due to the large positive tip potential. He ions are accelerated away from tip apex 187 along a plurality of trajectories. Two such trajectories 156 are shown in FIG. 13. As depicted in FIG. 13, trajectories 156 correspond to the left- and right-hand limits of the full width at half maximum (FWHM) trajectory distribution for the middle terminal shelf atom. As such, if trajectories 156 are extrapolated backwards (e.g., along lines 154) to the position of the middle terminal shelf atom, they define a virtual source 152 for the middle terminal shelf atom. The diameter of virtual source 152 is typically smaller than the diameter of the middle terminal shelf atom, and may be much smaller than the diameter of the middle terminal shelf atom (e.g., by a factor of 2 or more, a factor of 3 or more, a factor of 5 or more, a factor of 10 or more). Similar considerations apply to the other terminal shelf atoms, and each terminal shelf atom has a corresponding virtual source size.

The small virtual source size for terminal shelf atoms can provide a number of advantages. For example, the small virtual source size of ion beam 192 and the relatively small thickness of the ionization disk 148 from which ions in ion beam 192 arise can assist in ensuring that ion beam 192 has a relatively high brightness and a relatively narrow ion energy distribution.

Without wishing to be bound by theory, it is believed that using a tip temperature that is too low can negatively impact current stability and/or increase undesirable effects from increased impurity adsorption on the tip. In general, the temperature of tip 186 is 5K or more (e.g., 10 K or more, 25K or more, 50K or more 75K or more), and/or 100K or less (e.g., 90K or less, 80K or less). For example, the temperature of tip 186 can be from 5K to 100K (e.g., from 25K to 90K, from 50K to 90K, from 75K to 80K). The temperature of tip 186 can be attained by thermal coupling with a coolant, such as, for example, liquid helium or liquid nitrogen. Alternatively or additionally, tip 186 can be thermally cooled using a cryogenic refrigerator.

It is believed that, if the temperature of tip 186 is too low, the rate at which adsorbed He atoms are transported by moving to atoms 142 in the terminal atomic shelf of tip apex 187 is reduced so that not enough He atoms per unit time reach atoms 142 where they can be ionized. As a result, when the emission pattern of tip 186 is observed (e.g., by using field ion microscope (FIM) techniques, or by scanning FIM (SFIM) techniques), the abundance of ions from individual terminal shelf atoms alternates from relatively high abundance to relatively low abundance (commonly referred to as blinking). This can occur, for example, when there are no He atoms available for ionization in the vicinity of the terminal shelf atom at certain times. As the temperature of tip 186 is increased, the transport rate of He atoms toward the terminal shelf of atoms of tip apex 187 increases, and the observation of this alternating high/low abundance from terminal shelf atoms 142 is reduced or eliminated.

It is also believed that, if the temperature of tip 186 is too high, polarized He atoms will have too much kinetic energy to remain bound to tip 186 for sufficiently long periods of time to ensure efficient ionization of He atoms in the vicinity of terminal shelf atoms 142. This can also result in disappearance of the emission pattern from individual terminal shelf atoms as observed using FIM and/or SFIM imaging techniques. As a result, to ensure that the He ionization process at each of the terminal shelf atoms 142 produces stable ion currents from each of the terminal shelf atoms 142, the temperature of tip 186 is carefully controlled to mitigate against both undesirable high- and low-temperature effects.

In general, ion optics 130 are configured to direct ion beam 192 onto surface 181 of sample 180. As described in more detail below, ion optics 130 can, for example, focus, collimate, deflect, accelerate, and/or decelerate ions in beam 192. Ion optics 130 can also allow only a portion of the ions in ion beam 192 to pass through ion optics 130. Generally, ion optics 130 include a variety of electrostatic and other ion optical elements that are configured as desired. By manipulating the electric field strengths of one or more components (e.g., electrostatic deflectors) in ion optics 130, He ion beam 192 can be scanned across surface 181 of sample 180. For example, ion optics 130 can include two deflectors that deflect ion beam 192 in two orthogonal directions. The deflectors can have varying electric field strengths such that ion beam 192 is rastered across a region of surface 181.

When ion beam 192 impinges on sample 180, a variety of different types of particles 194 can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 150 and 160 are positioned and configured to each measure one or more different types of particles resulting from the interaction between He ion beam 192 and sample 180. As shown in FIG. 10, detector 150 is positioned to detect particles 194 that originate primarily from surface 181 of sample 180, and detector 160 is positioned to detect particles 194 that emerge primarily from surface 183 of sample 180 (e.g., transmitted particles). As described in more detail below, in general, any number and configuration of detectors can be used in the microscope systems disclosed herein. In some embodiments, multiple detectors are used, and some of the multiple detectors are configured to measure different types of particles. In certain embodiments, the detectors are configured to provide different information about the same type of particle (e.g., energy of a particle, angular distribution of a given particle, total abundance of a given particle). Optionally, combinations of such detector arrangements can be used.

In general, the information measured by the detectors is used to determine information about sample 180. Typically, this information is determined by obtaining one or more images of sample 180. By rastering ion beam 192 across surface 181, pixel-by-pixel information about sample 180 can be obtained in discrete steps. Detectors 150 and/or 160 can be configured to detect one or more different types of particles 194 at each pixel. Typically, a pixel is a square, although in some embodiments, pixels can have different shapes (e.g., rectangular). A pixel size, which corresponds to a length of a side of the pixel, can be, for example, from 100 pm to two μm (e.g., from one nm to one μm). In some embodiments, the location of adjacent pixels can be determined to within at least 200 pm (e.g., to within at least 100 pm, to within at least 75 pm, to within at least 50 pm). Thus, the operator of the system can determine the location of the center of the beam spot to within at least 200 pm (e.g., to within at least 100 pm, to within at least 75 pm, to within at least 50 pm). In certain embodiments, the field of view (FOV) of sample 180 is 200 nm or more (e.g., 500 nm or more, 1 μm or more, 50 μm or more, 100 μm or more, 500 μm or more, 1 mm or more, 1.5 mm or more), and/or 25 mm or less (15 mm or less, 10 mm or less, five mm or less). The field of view refers to the area of a sample surface that is imaged by the ion microscope.

The operation of microscope system 100 is typically controlled via electronic control system 170. For example, electronic control system 170 can be configured to control the gas(es) supplied by gas source 110, the temperature of tip 186, the electrical potential of tip 186, the electrical potential of extractor 190, the electrical potential of suppressor 188, the settings of the components of ion optics 130, the position of sample manipulator 140, and/or the location and settings of detectors 150 and 160. Optionally, one or more of these parameters may be manually controlled (e.g., via a user interface integral with electronic control system 170). Additionally or alternatively, electronic control system 170 can be used (e.g., via an electronic processor, such as a computer) to analyze the information collected by detectors 150 and 160 and to provide information about sample 180 (e.g., topography information, material constituent information, crystalline information, voltage contrast information, optical property information, magnetic information ), which can optionally be in the form of an image, a graph, a table, a spreadsheet, or the like. Typically, electronic control system 170 includes a user interface that features a display or other kind of output device, an input device, and a storage medium.

A. Overview

Figure 14:
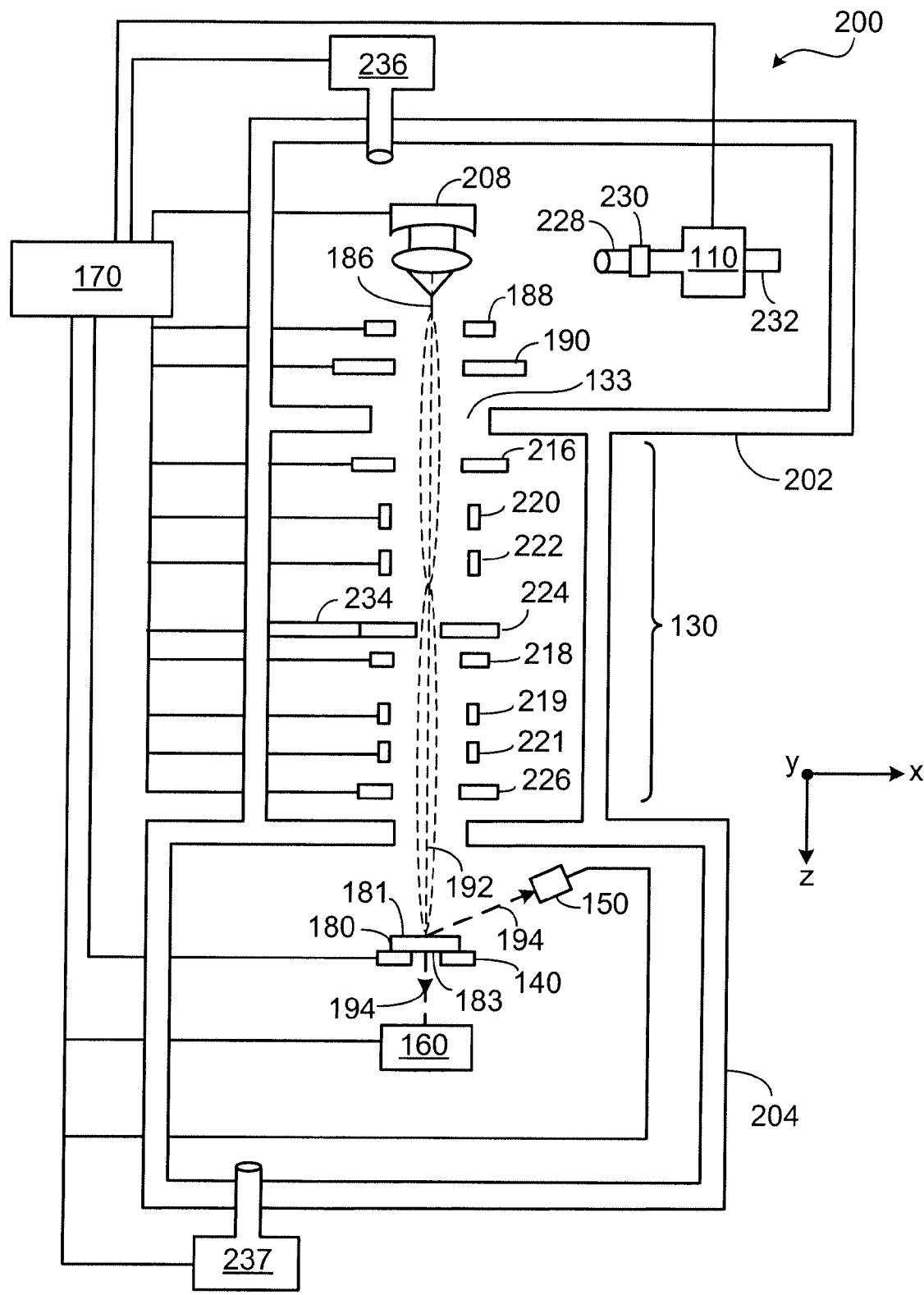
FIG. 14 is a schematic diagram of a helium ion microscope system.

FIG. 14 shows a schematic diagram of a He ion microscope system 200. Microscope system 200 includes a first vacuum housing 202 enclosing a He ion source and ion optics 130, and a second vacuum housing 204 enclosing sample 180 and detectors 150 and 160. Gas source 110 delivers He gas to microscope system 200 through a delivery tube 228. A flow regulator 230 controls the flow rate of He gas through delivery tube 228, and a temperature controller 232 controls the temperature of He gas in gas source 110. The He ion source includes a tip 186 affixed to a tip manipulator 208. The He ion source also includes an extractor 190 and a suppressor 188 that are configured to direct He ions from tip 186 into ion optics 130. Ion optics 130 include a first lens 216, alignment deflectors 220 and 222, an aperture 224, an astigmatism corrector 218, scanning deflectors 219 and 221, and a second lens 226. Aperture 224 is positioned in an aperture mount 234. Sample 180 is mounted in/on a sample manipulator 140 within second vacuum housing 204. Detectors 150 and 160, also positioned within second vacuum housing 204, are configured to detect particles 194 from sample 180. Gas source 110, tip manipulator 208, extractor 190, suppressor 188, first lens 216, alignment deflectors 220 and 222, aperture mount 234, astigmatism corrector 218, scanning deflectors 219 and 221, sample manipulator 140, and/or detectors 150 and/or

160 are typically controlled by electronic control system 170. Optionally, electronic control system 170 also controls vacuum pumps 236 and 237, which are configured to provide reduced-pressure environments inside vacuum housings 202 and 204, and within ion optics 130.

B. Ion Source

Figure 15:
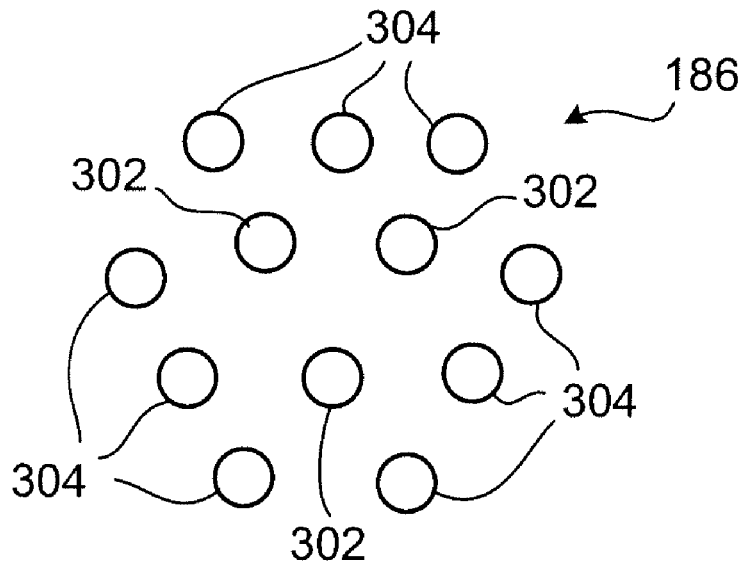
FIG. 15 is a schematic representation of an enlarged top view of an embodiment of a W(111) tip.
Figure 16:
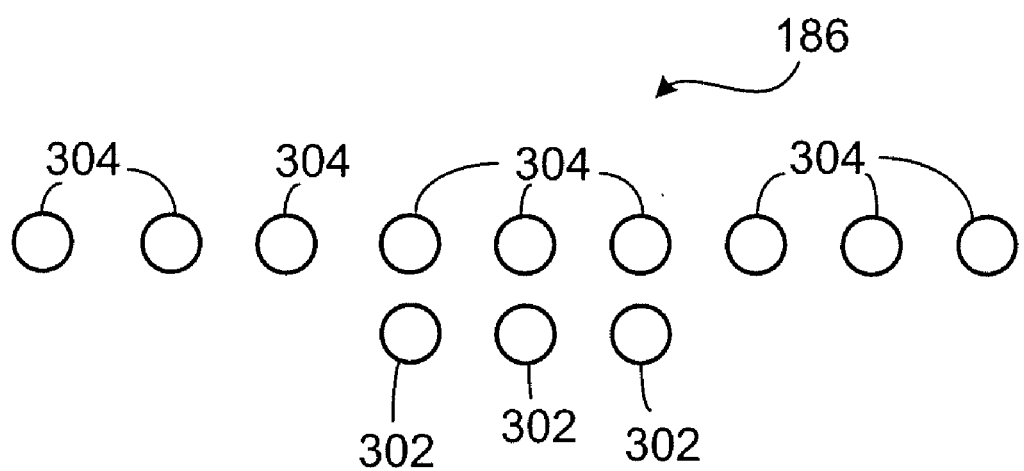
FIG. 16 is a schematic representation of an enlarged side view of the W(111) tip of FIG. 15.

As noted above, in general, tip 186 can be formed of any appropriate electrically conductive material. In certain embodiments, tip 186 can be formed of a single crystal material, such as a single crystal metal. Typically, a particular single crystal orientation of the terminal shelf of atoms of tip apex 187 is aligned with a longitudinal axis of tip 186 to within 3° or less (e.g., within 2° or less, within 1° or less). In some embodiments, apex 187 of tip 186 can terminate in an atomic shelf having a certain number of atoms (e.g., 20 atoms or less, 15 atoms or less, 10 atoms or less, nine atoms or less, six atoms or less, three atoms or less). For example, apex 187 of tip 186 can be formed of W(111) and can have a terminal shelf with three atoms (a trimer). FIGS. 15 and 16 show schematic representations of enlarged top and side views, respectively, of the two atomic shelves of a W tip 186 that are nearest to the apex of tip. The terminal shelf, which includes three W atoms 302 arranged in a trimer, corresponds to a (111) surface of W. Without wishing to be bound by theory, it is believed that this trimer surface is advantageous (in terms of its ease of formation, re-formation and stability) because the surface energy of the W(111) crystal face favorably supports a terminal shelf formed by three W atoms arranged in an equilateral triangle to form a trimer. The trimer atoms 302 are supported by a second shelf of W atoms 304.

In some embodiments, tip 186 can have a terminal shelf that includes fewer than three atoms or more than three atoms. For example, a W(111) tip can have a terminal shelf that includes two atoms, or a terminal shelf that includes only one atom. Alternatively, a W(111) tip can have a terminal shelf that includes four or more atoms (e.g., five or more atoms, six or more atoms, seven or more atoms, eight or more atoms, nine or more atoms, ten or more atoms, more than ten atoms).

Alternatively, or in addition, tips that correspond to other W crystalline orientations (e.g., W(112), W(110) or W(100)) can be used, and such tips can have terminal shelves that include one or more atoms (e.g., two or more atoms, three or more atoms, four or more atoms, five or more atoms, six or more atoms, seven or more atoms, eight or more atoms, nine or more atoms, ten or more atoms, more than ten atoms).

In some embodiments, tips formed from a material other than single crystal W can be used in the ion source (e.g., a single crystal of a metal, such as a single crystal of one of the metals noted above), and such tips can have terminal shelves that include one or more atoms (e.g., two or more atoms, three or more atoms, four or more atoms, five or more atoms, six or more atoms, seven or more atoms, eight or more atoms, nine or more atoms, ten or more atoms, more than ten atoms).

As described below, the shape of tip apex 187 can have an impact on the quality of the ion beam, which can have an impact on the performance of microscope system 200. For example, when viewed from the side, tip apex 187 can be symmetrically formed about its longitudinal axis, or it can be asymmetrically formed about its longitudinal axis. In certain embodiments, from one or more side views, tip apex 187 may be symmetrically formed about its longitudinal axis, and, from one or more different side views, tip apex 187 may be asymmetrically formed about its longitudinal axis.

Figure 17:
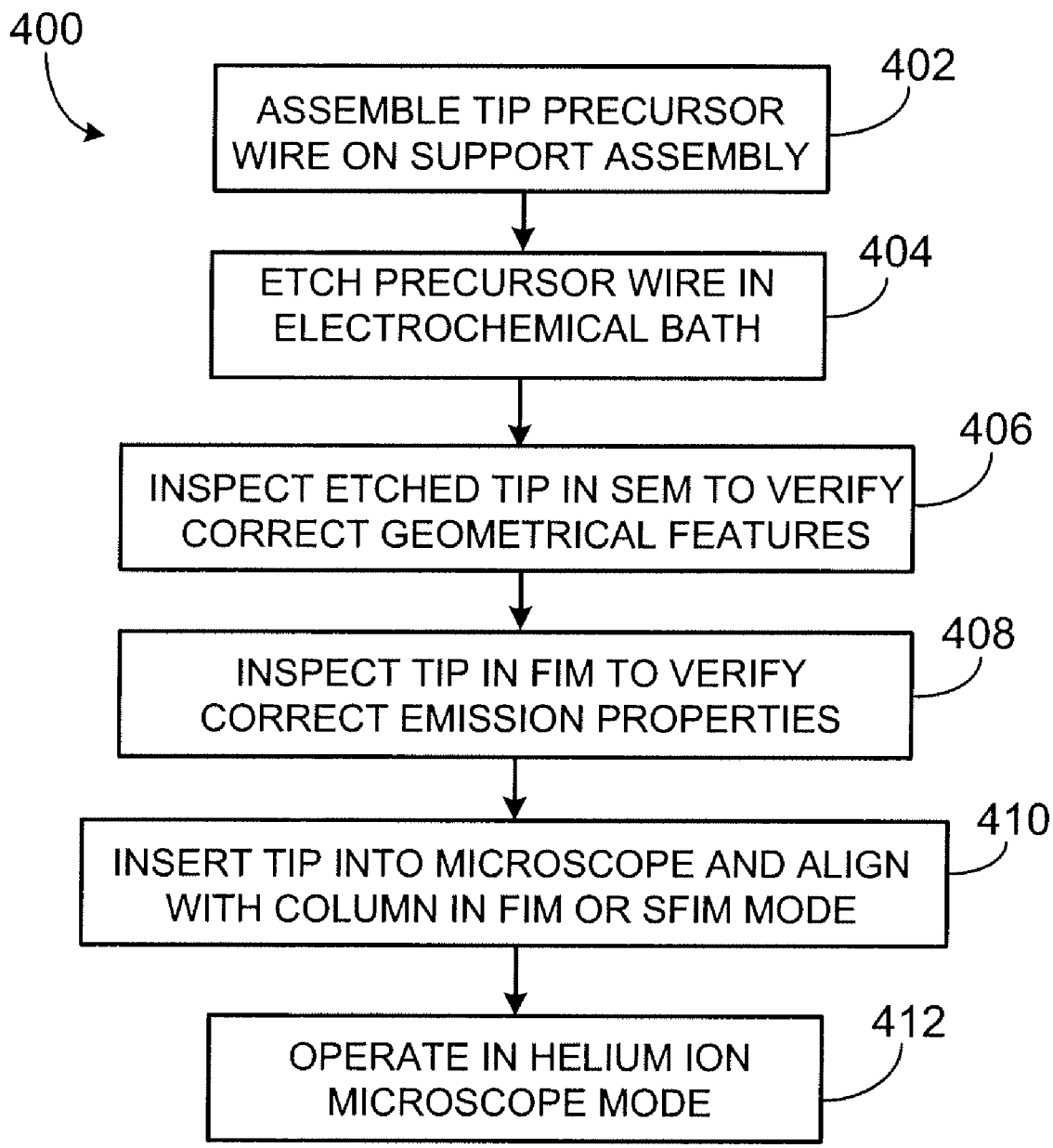
FIG. 17 is a flow chart showing an embodiment of a method of making a tip.

FIG. 17 is a flow chart for a process 400 of making a W(111) tip having a terminal atomic shelf that is a trimer. In a first step 402, a single crystal W(111) precursor wire is attached to a support assembly. In a second step 404, the precursor wire is etched in an electrochemical bath to shape the tip of the wire. Then, in step 406 of process 400, the etched tip is examined to verify that the tip has suitable geometrical features. Determination of geometrical features typically includes obtaining profile images of the etched tip and calculating various geometrical parameters from data obtained from the profile images. The inspection can be performed using a SEM, for example.

Subsequently, in step 408, the terminal shelf of the apex of the tip of the etched wire is formed into a trimer. This process generally involves imaging the tip (e.g., using FIM or SFIM) and shaping the tip (e.g., using field evaporation). Then, in step 410 of process 400, apex 187 of tip 186 is aligned within system 200. With the support assembly installed in microscope system 200, microscope system 200 is evacuated using one or more vacuum pumps, and then heat is applied to tip 187 to remove, for example, oxides, condensates, and/or any other impurities that may have adhered to the tip surface. Typically, for example, tip 186 is heated to a temperature of 900 K or more (e.g., 1000 K or more, 1100 K or more) for a duration of 10 s or more (e.g., 30 s or more, 60 s or more). Heating may also assist in re-faceting tip 186, in the event that the tip shape is compromised by the presence of impurities.

With tip 186 aligned within system 200, and the He ion beam aligned so that a portion of ion beam 192 passes through aperture 224, microscope system 200 can be operated in He ion mode in step 412 of process 400.

To verify the integrity of tip 186, the field emission pattern from tip 186 can be periodically monitored by operating microscope system 200 in FIM or SFIM mode. If the trimer structure remains intact at tip apex 187, then tip 186 can continue to be used to provide ion beam 192 to microscope system 200. However, under certain circumstances, FIM or SFIM imaging of tip 186 may reveal that the trimer structure is no longer intact on tip apex 187. In this case, tip 186 can first be field evaporated to round the tip and remove the damaged trimer structure, and then re-sharpened in situ (e.g., without removing tip 186 from microscope system 200) using a process as described above. Methods of forming and inspecting tips, and aligning tips in microscope systems, are disclosed, for example, in previously-incorporated U.S. patent application Ser. No. 11/600,711 entitled "ION SOURCES, SYSTEMS AND METHODS" by Billy W. Ward et al., filed on Nov. 15, 2006, now published as U.S. Publication No. US 2007/0158558.

Figure 18:
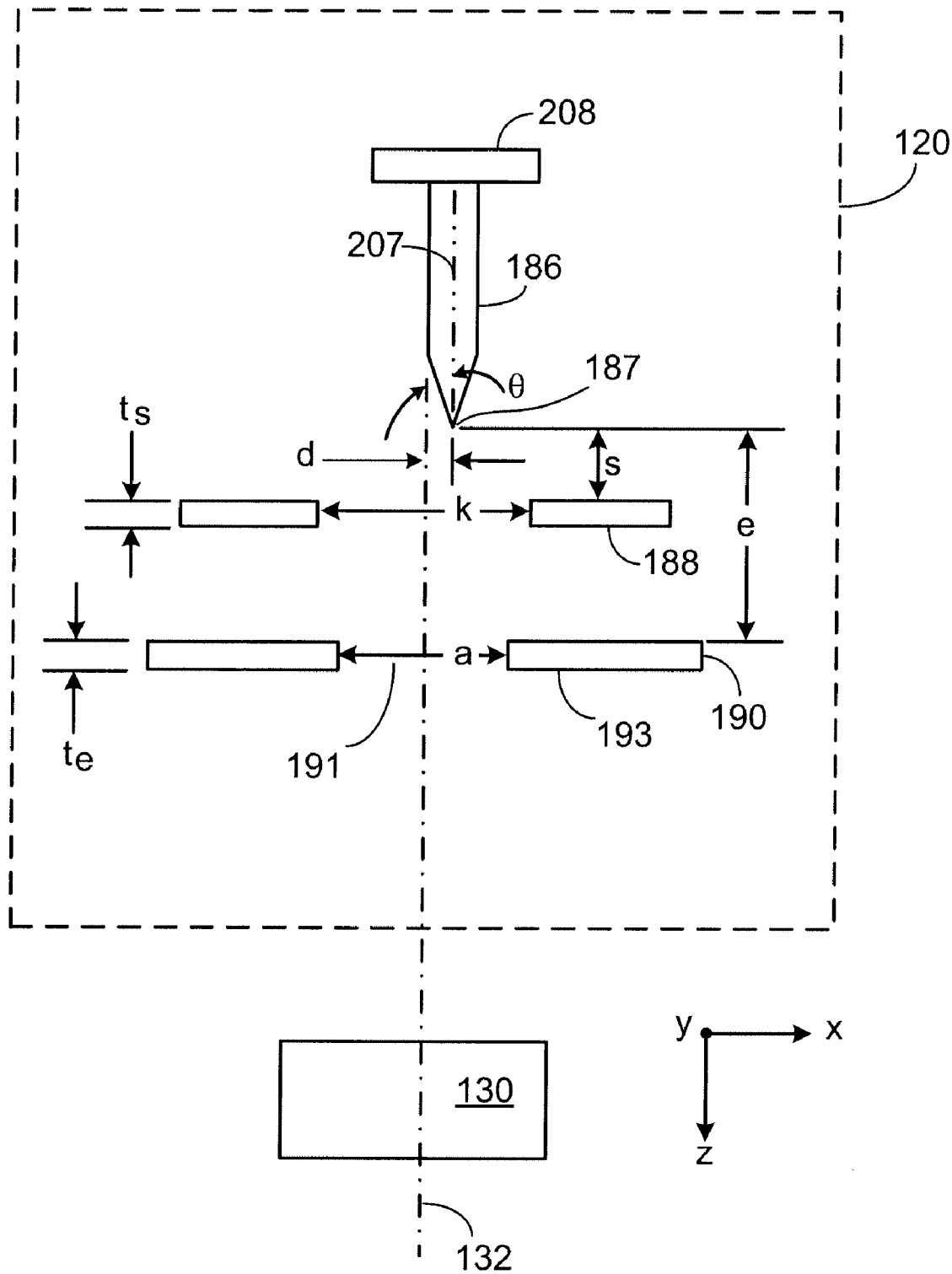
FIG. 18 is a schematic view of an embodiment of a gas field ion source and ion optics.

Referring to FIG. 18, alignment of tip 186 in microscope system 200 includes aligning a longitudinal axis 207 of tip 186 with a longitudinal axis 132 of ion optics 130 so that the distance d between axes 207 and 132 at apex 187 of tip 186 is less than 2 mm (e.g., less than 1 mm, less than 500 µm, less than 200 µm). In some embodiments, the angle between axes 207 and 132 at apex 187 of tip 186 is 2° or less (e.g., 1° or less, 0.5° or less, 0.2° or less).

Extractor 190 includes an opening 191. In general, the shape of extractor 190 and of opening 191 can be selected as desired. Typically, these features are chosen to ensure that He ions are efficiently and reliably directed into ion optics 130. In some embodiments, extractor 190 is positioned further in the +z direction than tip 186, as shown in FIG. 18. In certain embodiments, extractor 190 is positioned further in the −z direction than tip 186. In such embodiments, for example, tip 186 protrudes through extractor 190 and extends further along the z-axis in the +z direction than extractor 190. While extractor 190 is shown as having a particular configuration in FIG. 18, more generally, extractor 190 can be of any desired design. For example, in some embodiments, opening 191 can have curved sides of any desired shape.

Extractor 190 can generally be biased either positively or negatively with respect to tip 186. In some embodiments, the electrical potential applied to extractor 190 is −10 kV or more (e.g., −5 kV or more, 0 kV or more), and/or 20 kV or less (e.g., 15 kV or less, 10 kV or less) with respect to tip 186.

Optionally, suppressor 188 can also be present in the vicinity of tip 186. Suppressor 188 can be used, for example, to alter the electric field distribution in the vicinity of tip 186 by adjusting the potential applied to suppressor 188. Together with extractor 190, suppressor 188 can be used to control the trajectory of He ions produced at tip 186. In certain embodiments, as shown in FIG. 18, suppressor 188 is positioned further along in the +z-direction than tip 186. In some embodiments, tip 186 is positioned further along in the +z-direction than suppressor 188, so that tip 186 extends through suppressor 188 in the +z-direction.

In general, microscope system 200 can be configured so that after passing through extractor 190, the energy of the ions in ion beam 192 can be selected as desired. Typically, the average energy of the ions in ion beam 192 is 5 keV or more (e.g., 10 keV or more, 20 keV or more, 30 keV or more) and/or 100 keV or less (e.g., 90 keV or less, 80 keV less, 60 keV or less, 50 kV or less, 40 kV or less, 30 kV or less) after passing through entry opening 133 to ion optics 130. For example, in some embodiments, after passing through entry opening 133, the energy of the ions in ion beam 192 is from 5 keV to 100 keV (e.g., from 10 keV to 90 keV, from 20 keV to 80 keV). For example, in embodiments where it is desirable to detect ions that are transmitted through a sample, higher ion energies (e.g., 50 keV to 100 keV) may be used.

Further, in certain embodiments, the energy of the ions in ion beam 192 can be changed without changing the ion current. That is, the electrical potential applied to tip 186 can be adjusted to modify the average energy of ion beam 192 without substantially changing the ion beam current from ion beam 192.

Ion optics 130 generally include one or more elements such as lenses, deflectors, and filters, that can be used to collimate, focus, deflect, and shape the ion beam emerging from ion source 120 prior to the beam impinging on a sample.

Exemplary dimensions, voltages, and other settings for various components of microscope system 200 are disclosed, for example, in previously-incorporated U.S. patent application Ser. No. 11/600,711 entitled "ION SOURCES, SYSTEMS AND METHODS" by Billy W. Ward et al., filed on Nov. 15, 2006, now published as U.S. Publication No. US 2007/0158558.

C. Detectors

Detectors 150 and 160 are depicted schematically in FIG. 14, with detector 150 positioned to detect particles from surface 181 of sample 180 (the surface on which the ion beam impinges), and detector 160 positioned to detect particles from surface 183 of sample 180. In general, a wide variety of different detectors can be employed in microscope system 200 to detect different particles, and a microscope system 200 can typically include any desired number of detectors. The configuration of the various detector(s) can be selected in accordance with particles to be measured and the measurement conditions. In some embodiments, a spectrally resolved detector may be used. Such detectors are capable of detecting particles of different energy and/or wavelength, and resolving the particles based on the energy and/or wavelength of each detected particles. In certain embodiments, a spectrally resolved detector includes componentry capable of directing particles to different regions of the detector based on the energy and/or wavelength of the particle.

Certain exemplary detectors and arrangements of detectors are described below. Detection systems and methods are also generally disclosed, for example, in previously-incorporated U.S. patent application Ser. No. 11/600,711 entitled "ION SOURCES, SYSTEMS AND METHODS" by Billy W. Ward et al., filed on Nov. 15, 2006, now published as U.S. Publication No. US 2007/0158558.

(i) Everhart-Thornley Detectors

Figure 19:
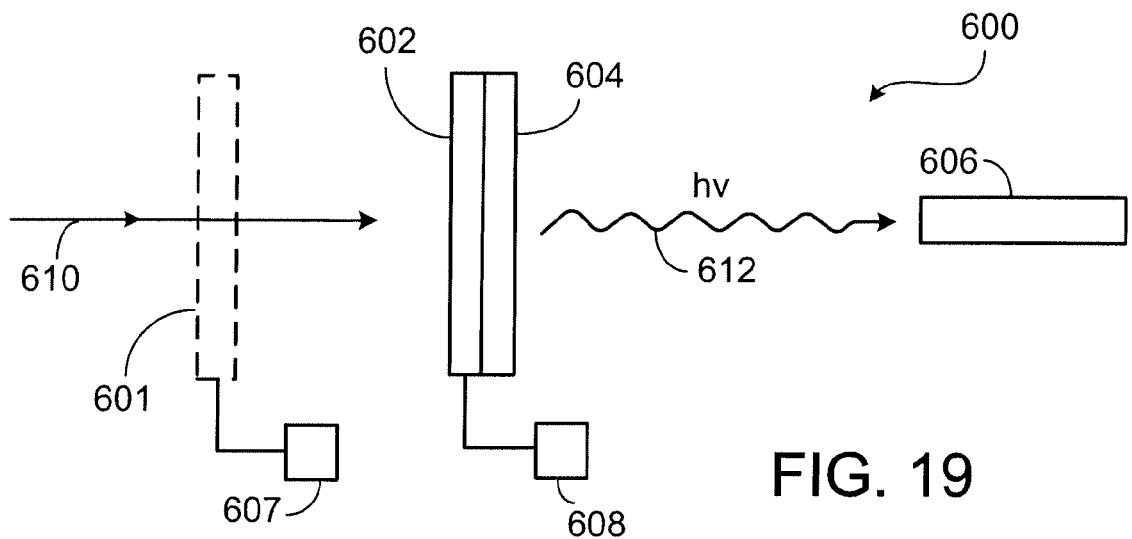
FIG. 19 is a schematic diagram of an Everhart-Thornley detector.

An Everhart-Thornley (ET) detector can be used to detect secondary electrons, ions, and/or neutral particles. FIG. 19 shows a schematic diagram of an ET detector 600 that includes a particle selector 601, a conversion material 602, a support 604, a photon detector 606, and voltage sources 607 and 608.

During operation, voltage source 607 applies a voltage of relatively small magnitude (e.g., 500 V or less, such as from 100 V to 500 V) to particle selector 601 (formed of a conductive material), and voltage source 608 applies a voltage of relatively large magnitude (e.g., 5 kV or more, 10 kV or more) to conversion material 602. In embodiments in which the ET detector is used to measure electrons from sample 180 (e.g., secondary electrons), the sign of the voltage applied to particle selector 601 and conversion material 602 is positive with respect to sample 180. In embodiments in which the ET detector is used to measure ions from sample 180 (e.g., secondary ions, scattered ions), the sign of the voltage applied to particle selector 601 and conversion material 602 is negative with respect to sample 180. In certain embodiments, sample 180 can also be biased (with respect to the common external ground) to assist in delivering particles from sample 180 to detector 600. For example, when the ET detector is used to measure secondary electrons from sample 180, the sample can be negatively biased relative to the common external ground. Applying a negative potential bias to manipulator 140 may be particularly useful, for example, when detecting secondary electrons generated in a high aspect ratio (e.g., deep) hole or via in the sample. The negative potential bias relative to the common external ground can assist in accelerating electrons out of the hole or via and away from the sample, making detection of the electrons easier. In the absence of the negative bias, many of the secondary electrons might instead re-enter the sample at points along the hole or via walls, never escaping the hole or via to be detected.

Sample 180 can be positively biased, for example, when the ET detector is used to measure ions from the sample. The magnitude of the electrical potential applied to bias the sample can be 5 V or more (e.g., 10 V or more, 15 V or more, 20 V or more, 30 V or more, 50 V or more, 100 V or more).

Charged particles 610 (e.g., electrons or ions) from sample 180 are attracted to particle selector 601, pass through particle selector 601, and are accelerated toward conversion material 602. Charged particles 610 then collide with conversion material 602, generating photons 612. Photons 612 pass through support 604 and are detected by photon detector 606.

An ET detector can be located at any position relative to sample 180 to detect neutral or charged particles. Typically, for example, an ET detector is positioned adjacent to second lens 226 of ion optics 130. Optionally, an ET detector can also be positioned such that it is tilted downward slightly towards sample 180 (e.g., in a similar configuration as that depicted for detector 150 in FIG. 14).

In certain embodiments, an ET detector can be positioned in the vicinity of surface 183 of sample 180. Such a configuration may be desirable, for example, when seeking to measure secondary electrons from sample 180 that emerge from surface 183 (e.g., after being transmitted through sample 180). In such embodiments, the ET detector can have a configuration that is similar to the configuration of detector 160 in FIG. 14.

(ii) Microchannel Plate Detectors

In some embodiments, a microchannel plate detector can be used to amplify a flux of secondary electrons, neutral atoms, or ions from a sample. Microchannel plates are typically formed from materials such as fused silica, and generally include a large number of small diameter channels arranged in the form of an array. Particles enter individual channels and collide with channel walls, generating free electrons. Typically, multiple free electrons are generated on each collision of a particle (neutral atom, ion, or electron) with a channel wall. As a result, a cascaded electron signal corresponding to an amplification of the input particle signal exits the microchannel plate.

Microchannel plate-based detectors (which can include one or more microchannel plates) can be configured to detect ions, secondary electrons, and/or neutral atoms from sample 180. Neutral particles and/or ions (e.g., secondary ions and atoms, scattered ions and primary atoms) formed from sample 180 typically leave surface 181 of sample 180 (the surface on which the ion beam impinges). Accordingly, microchannel plate-based detectors configured to measure neutrals and/or ions from sample 180 are generally located at positions similar to the position of detector 150 depicted in FIGS. 10 and 14. However, in certain embodiments, neutral particles and/or ions (e.g., transmitted ions) can be investigated. In such embodiments, a microchannel plate-based detector can be located at positions similar to the position of detector 160 in FIGS. 10 and 14. Secondary electrons can be detected either from surface 181 (the surface on which the ion beam impinges) and/or surface 183 of sample 180 (the surface on the opposite side from where the ion beam impinges), and microchannel plate-based detectors configured to detect secondary electrons from sample 180 are located at positions similar to detector 150 and/or detector 160 as depicted in FIGS. 10 and 14.

Microchannel plates amplify an incoming particle signal and convert the incoming signal to an outgoing electron signal. To visualize the outgoing electron signal, microchannel plate-based detectors can also include a conversion material, a screen, and a photon detector (see discussion above).

Figure 20:
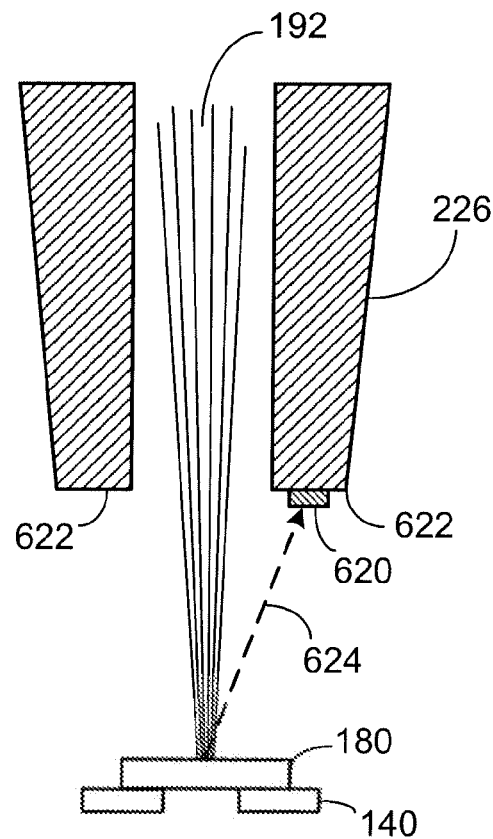
FIG. 20 is a cross-sectional view of a portion of a gas field ion microscope system including a microchannel plate detector.

In some embodiments, microchannel plates are affixed directly to elements of ion optics 130. FIG. 20 shows a cross-sectional view of a microchannel plate detector 620 mounted directly to an electrostatic lens 226. Lens 226 has a conical shape, with a flat lower surface 622. Detector 620 is mounted directly to surface 622. When sample 180 is exposed to ion beam 192, ions, secondary electrons, and/or neutral atoms from sample 180 (collectively indicated by arrow 624) can be detected by microchannel plate detector 620. Detector 620 registers a current that is proportional to the detected particle flux, which can be conveyed to electronic control system 170.

(iii) Conversion Plates

In some embodiments, a conversion plate can be used to detect ions (e.g., scattered ions, secondary ions) from a sample or neutral particles (e.g., primary neutral He atoms) from the sample. Typically, a conversion plate can be formed from a thin foil material that, when struck by an incident ion or atom, has a high secondary electron yield. An example of such a material is platinum. The secondary electron yield produces an abundance of secondary electrons that are readily detected, for example, by an appropriate electron detector configured, for example, as detectors 150 and/or 160 (FIGS. 10 and 14).

(iv) Channeltron Detectors

Channeltron detectors can also be used to detect particles such as electrons, ions and neutral atoms leaving a sample. Channeltron detectors function by amplifying particle signals through multiple internal collisions in a manner similar to that described in connection with microchannel plate detectors. Measurement of relatively weak secondary electron, ion, or neutral atom fluxes from sample 180 is possible by measuring the amplified particle signals that are output by a channeltron detector (e.g., using electronic control system 170). When measuring secondary electrons from sample 180, a channeltron detector can be located in a position similar to that depicted for detector 150 and/or detector 160 in FIGS. 10 and 14. Typically, for the measurement of ions and/or neutral particles from sample 180, a channeltron detector is located in a position similar to the position of detector 150 and/or the position of detector 160 as depicted in FIGS. 10 and 14.

(v) Phosphor Detectors

Phosphor-based detectors, which include a thin layer of a phosphor material deposited atop a transparent substrate, and a photon detector such as a CCD camera, a PMT, or one or more diodes, can be used to detect electrons, ions and/or neutral particles from a sample. Particles strike the phosphor layer, inducing emission of photons from the phosphor which are detected by the photon detector. Phosphor-based detectors can be arranged in positions similar to those of detector 150 and/or detector 160 as depicted in FIGS. 10 and 14, depending upon the type of particle that is measured (see discussion above).

(vi) Solid State Detectors

Solid state detectors can be used to detect secondary electrons, ions, and/or neutral atoms from a sample. A solid state detector can be constructed from a sensor formed of a material such as silicon, or a doped silicon material. When incident particles strike the sensor, electron-hole pairs are created in the sensor material, producing a current that can be detected by electronic control system 170. The number of electron-hole pairs generated by an incident particle, and therefore the corresponding magnitude of the current produced, depends in part upon the particle's energy. Thus, a solid state detector can be particularly useful for energy measurements of particles, which can be especially advantageous when detecting high energy particles (e.g., scattered He ions and neutral He atoms) from sample 180.

(vii) Scintillator Detectors

Similar to phosphor-based detectors, scintillator-based detectors include a scintillator material that generates photons in response to being struck by an incident particle (electron, ion, or neutral atom). Suitable scintillator materials include, for example, YAG and YAP. The photon yield in scintillator-based detectors depends on the energy of the incident particles. As a result, a scintillator detector can be particularly useful for energy measurements of particles, which can be especially advantageous when detecting high energy particles (e.g., scattered He ions and neutral He atoms) from sample 180.

(viii) Energy Detectors for Ions

A variety of different detectors and detection schemes can be implemented to measure energies of ions (e.g., scattered He ions) from a sample. Electrostatic prism detectors, in which an electric and/or magnetic field is used to deflect incident ions, where the amount of deflection depends on the energy of the ions, can be used to spatially separate ions with different energies. Magnetic prism detectors may also be used to spatially separate ions based on the energy of the ions. Any of the suitable detectors discussed above (e.g., microchannel plates, channeltrons, and others) can then be used to detect the deflected ions.

Quadrupole detectors can also be used to analyze energies of ions from a sample. In a quadrupole detector, a radio-frequency (RF) field within the quadrupole ensures that ions having a chosen mass and energy propagate along a straight, undeflected trajectory within the quadrupole. Ions with a different mass and/or energy propagate along a curved trajectory within the quadrupole. From the deflected position of ions within the quadrupole analyzer, energies of the ions can be determined.

In some embodiments, ion energy can be determined by placing a positively biased particle selector (e.g., a screen or mesh of electrically conductive material, or a cylindrical metal tube or ring) along the flight path of the ions and in front of the detector. The magnitude of the electrical potential applied to particle selector 601 can initially be very high (e.g., a value certain to prevent ions from sample 180 from passing therethrough), and the magnitude of the electrical potential can be reduced while using an appropriate detector (see discussion above) to detect the ions. The current of ions that reach the detector as a function of the magnitude of the potential bias on the particle selector can be used to determine information about the energy of the ions.

(ix) Energy Detectors for Electrons

A variety of different detectors and detection schemes can be implemented to measure energies of electrons (e.g., secondary electrons) from a sample. Prism detectors, in which an electric and/or magnetic field is used to deflect incident electrons, and where the amount of deflection depends on the energy of the electrons, can be used to spatially separate electrons with different energies. Any of the suitable detectors discussed above can then be used to detect the deflected electrons.

In some embodiments, electron energies can be determined by placing a negatively biased particle selector (e.g., a screen or mesh of electrically conductive material, or a cylindrical metal tube or ring) along the flight path of the electrons and in front of the detector. The magnitude of the electrical potential of the particle selector can initially be very high (e.g., a value certain to prevent the electrons from sample 180 from passing therethrough), and the magnitude of the electrical potential can be reduced while using an appropriate detector (see discussion above) to detect the electrons. The electron current that reaches the detector as a function of the magnitude of the applied electrical potential on the particle selector can be used to determine information about the energies of the electrons.

(x) Time-of-Flight Detectors

The detectors disclosed above can also be configured to measure time-of-flight information for secondary electrons, ions, and neutral atoms. To perform time-of-flight detection, ion beam 192 is operated in pulsed mode. Ion beam 192 can be pulsed, for example, by rapidly changing the electrical potentials applied to one or more beam deflectors. By increasing these potentials, for example, ion beam 192 can be diverted from its usual path in ion optics 130 such that ion beam 192 is temporarily blocked by aperture 224. If the potentials of the deflectors are then returned to their normal values for a short time before being increased again, a pulse of He ions can be delivered to sample 180.

At the same time, detectors 150 and 160 can be synchronized to a clock signal from electronic control system 170 that is based upon the temporal variation in potentials applied to the deflectors. As a result, the time interval between the launch of a He ion pulse and the detection of particles from sample 180 can be accurately measured. From known information about the time of propagation of the He ion pulse within ion optics 130, the time-of-flight of the detected particles between sample 180 and detectors 150 and/or 160 can be determined.

(xi) Angle-Dependent Measurements

In addition to measuring relative abundances and energies of particles from a sample, angle-dependent scattering information can be obtained using the detectors disclosed above. Typically, to acquire angle-dependent information, a detector is affixed to a mount (e.g., a swivel mount) that permits movement of the detector throughout a range of solid angles about sample 180. At a given orientation with respect to sample 180 that corresponds to a particular solid angle, abundance and/or energy measurements of particles are recorded. The detector is sequentially re-positioned at different solid angles and the measurements are repeated to determine the angular dependence of the measured quantities. In some embodiments, a limiting aperture such as a pinhole can be placed in front of the detector in the path of the scattered particles to further restrict the range of angles over which measurement of particles from sample 180 occurs.

D. Operational Parameters

Figure 21A:
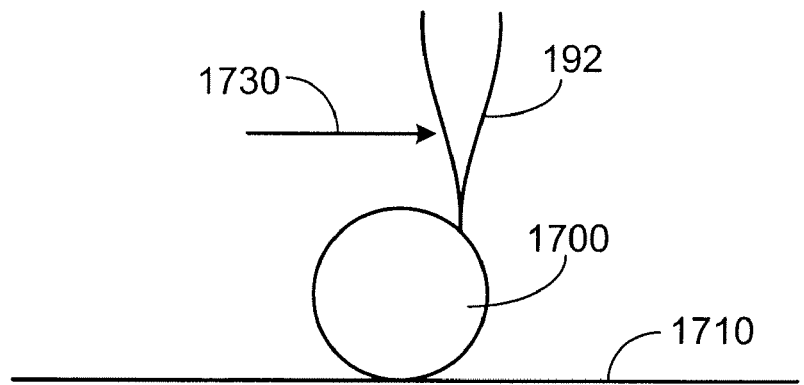
FIGS. 21A and 21B are side and top views of a gold island supported by a carbon surface.
Figure 21B:
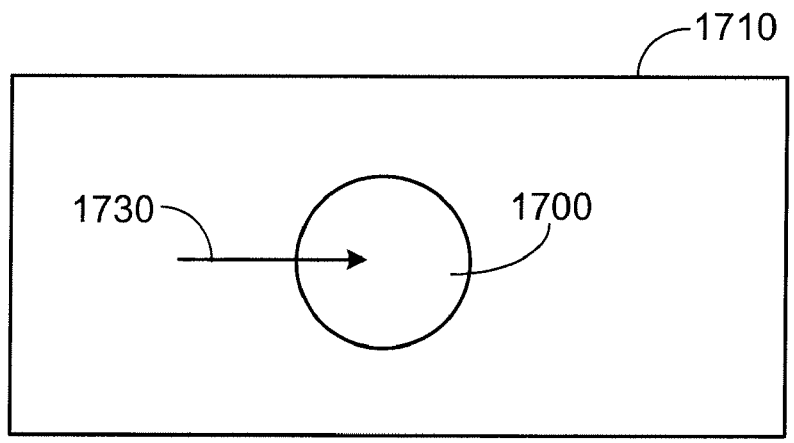
Figure 21C:
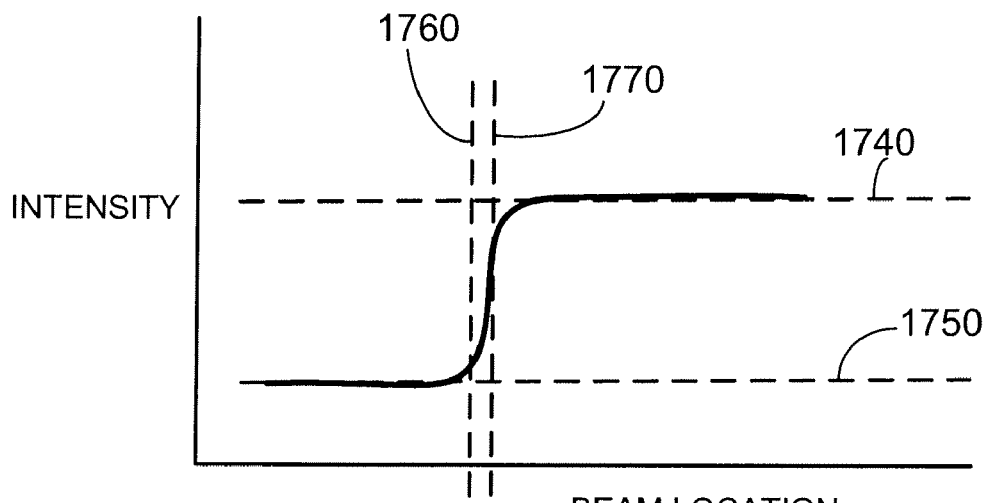
FIG. 21C is a plot of average measured secondary electron total abundance as a function of ion beam position for the sample of FIGS. 21A and 21B.

Ion beam 192 can have a relatively small spot size on surface 181 of sample 180. For example, in some embodiments, the spot size of ion beam 192 on surface 181 of sample 180 can have a dimension of 10 nm or less (e.g., nine nm or less, eight nm or less, seven nm or less, six nm or less, five nm or less, four nm or less, three nm or less, two nm or less, one nm or less). In certain embodiments, the spot size of ion beam 192 on surface 181 of sample 180 has a dimension of 0.05 nm or more (e.g., 0.1 nm or more, 0.2 nm or more, 0.25 nm or more, 0.5 nm or more, 0.75 nm or more, one nm or more, two nm or more, three nm or more). In some embodiments, the spot size of ion beam 192 on surface 181 has a dimension of from 0.05 nm to 10 nm (e.g., from 0.1 nm to 10 nm, 0.2 nm to 10 nm, 0.25 nm to 3 nm, 0.25 nm to one nm, 0.1 nm to 0.5 nm, 0.1 nm to 0.2 nm). As used herein, spot size is determined as follows with reference to FIGS. 21A-21C. An island 1700 formed of gold and having a dimension of from 50 nm to 2000 nm is disposed on a carbon surface 1710. The gold island is formed, for example, by vapor deposition of gold onto the carbon surface. Measurement samples that include gold islands deposited on carbon, suitable for the resolution measurements described herein, are available commercially from Structure Probe Inc. (West Chester, Pa.), for example. The ion microscope is operated such that it moves ion beam 192 linearly across a portion of the gold island, as well as the portions of the carbon surface on one side of the gold island (arrow 1730). The intensity of secondary electrons is measured as a function of the location of the ion beam (FIG. 21C). Asymptotic lines 1740 and 1750 are calculated (or drawn) corresponding to the average total abundance values for the carbon and gold, and vertical lines 1760 and 1770 are calculated (or drawn) corresponding to the locations where the total abundance is 25% and 75%, respectively, of the abundance difference between asymptotic lines 1740 and 1750. The spot size of ion microscope 200 is the distance between lines 1760 and 1770.

In general, the current of ion beam 192 at surface 181 of sample 180 is one nA or less (e.g., 100 pA or less, 50 pA or less), and/or 0.1 fA or more (e.g., one fA or more, 10 fA or more, 50 fA or more, 100 fA or more, one pA or more, 10 pA or more). For example, in some embodiments, the current of ion beam 192 at surface 181 of sample 180 is from 0.1 fA to one nA (e.g., from 10 fA to 100 pA, from 100 fA to 50 pA). In certain embodiments, it can be desirable to use a relatively low beam current when imaging a sample. For example, in some biological and/or pharmaceutical applications, it may be more important to use a low current to image in the sample (e.g., to reduce possible damage to the sample). In such embodiments, one current can be used to prepare the gas field ion microscope for use (e.g., a current of 10 fA or more), and a different current can be used to image the sample (e.g., a current of less than one fA, such as 0.1 fA).

Ion beam 192 can have a relatively high brightness at surface 181 of sample 180. For example, ion beam 192 can have a brightness of $1 \times 10^9$ A/cm$^2$sr (e.g., $1 \times 10^{10}$ A/cm$^2$sr or more, $1 \times 10^{11}$ A/cm$^2$sr or more) at surface 181 of sample 180. In some embodiments, the brightness can be increased by increasing the gas pressure adjacent to tip 186 and/or decreasing the temperature of tip 186. As referred to herein, the brightness of an ion beam is measured as follows. The FWHM of the distribution of ion trajectories in ion beam 192—in a region of space between extractor 190 and first lens 216 where the net electric field is relatively small and the ion trajectories are nearly straight lines—is determined in both the x- and y-directions. A total of 100 ion trajectories that fall within the FWHM width in both the x- and y-directions are chosen at random from the distribution of ion trajectories in ion beam 192. Each of the 100 ion trajectories is nearly a straight line, and is projected back toward tip apex 187. The spatial extent of the trajectories at a particular point $z_t$ along the z-axis is assessed by constructing, in a plane $Z_t$ parallel to the x-y plane and passing through point $z_t$, the smallest-diameter circle that encloses all of the points of intersection of the back-propagated trajectories with the plane $Z_t$. The diameter of the smallest-diameter circle is $d_s$. Typically, for points $z_t$ closer to tip apex 187, $d_s$ will be smaller and for points $z_t$ closer to sample 180, $d_s$ will be larger. At a particular point $z_t = z_0$, $d_s$ will be a minimum value $d_0$. That is, the spatial extent of the trajectories in a plane parallel to the x-y plane will be a minimum. The diameter $d_0$ of the minimum-diameter circle at point $z_0$ is referred to as the virtual source size of microscope system 200. Next, the divergence and beam current of ion beam 192 in the FWHM region of ion beam 192 between extractor 190 and first lens 216, as discussed above, are measured. Finally, brightness is calculated as beam current divided by the product of the virtual source size and the solid divergence angle of ion beam 192.

Ion beam 192 can have a relatively high reduced brightness at surface 181 of sample 180. For example, ion beam 192 can have a reduced brightness of $5 \times 10^8$ A/m$^2$srV or more (e.g., $1 \times 10^9$ A/cm$^2$srV or more, $1 \times 10^{10}$ A/cm$^2$srV or more) at surface 181 of sample 180. As referred to herein, the reduced brightness of an ion beam is the brightness of the ion beam divided by the average energy of the ions in the ion beam at the position where the beam current is measured Ion beam 192 can have a relatively low etendue at a distal end 193 of extractor 190. For example, ion beam 192 can have an etendue of $5 \times 10^{-21}$ cm$^2$sr or less (e.g., $1 \times 10^{-22}$ cm$^2$sr or less, $1 \times 10^{-23}$ cm$^2$sr or less, $1 \times 10^{-23}$ cm$^2$sr or less, $1 \times 10^{-24}$ cm$^2$sr or less) at distal end 193 of extractor 190. As referred to herein, the etendue of an ion beam is calculated as the mathematical product of the reciprocal of the brightness and the beam current.

Ion beam 192 can have a relatively low reduced etendue at a distal end 193 of extractor 190. For example, ion beam 192 can have a reduced etendue of $1 \times 10^{-16}$ cm$^2$sr or less (e.g., $1 \times 10^{-17}$ cm$^2$sr or less, $1 \times 10^{-18}$ cm$^2$sr or less, $1 \times 10^{-19}$ cm$^2$sr or less) at distal end 193 of extractor 190. Reduced etendue of an ion beam is the mathematical product of the etendue of the ion beam and the ratio of the average energy-to-charge of ions in the ion beam at the position where the beam current is measured.

Ion beam 192 can have a relatively low angular convergence with respect to surface 181 of sample 180. For example, in some embodiments, the convergence half angle of ion beam 192 can be 5 mrad or less (e.g., 1 mrad or less, 0.5 mrad or less, 0.1 mrad or less), and/or 0.05 mrad or more. As referred to herein the convergence half angle of an ion beam is determined as follows. A sample that includes a gold island atop a carbon substrate, as described above, is mounted in ion microscope 200 and translated in the z-direction so that the position of the focus of ion beam 192 lies, as nearly as possible, at the highest elevation point along a diameter of the gold island. Ion beam 192 is then translated linearly along the diameter of the gold island and the focused spot size, $s_f$, of the ion beam is measured, as described above. The sample is then translated in the +z direction, away from ion optics 130, by $s_z = 1$ μm, and ion beam 192 is translated linearly along the same diameter of the gold island to measure the defocused spot size, $s_d$, of ion beam 192. The convergence angle η can then be determined trigonometrically from the measurements of the focused and defocused spot sizes, along with the translation distance, as $$\eta = 2\sin^{-1}\left(\frac{s_d - s_f}{2s_z}\right) \qquad (3)$$

The convergence half angle of ion microscope 200 is η/2.

Ion microscope 200 can have a relatively good resolution. For example, in some embodiments, the resolution of ion microscope 200 can be 10 nm or less (e.g., nine nm or less, eight nm or less, seven nm or less, six nm or less, five nm or less, four nm or less, three nm or less, two nm or less, one nm or less). In certain embodiments, the resolution of ion microscope 200 can be 0.05 nm or more (e.g., 0.1 nm or more, 0.2 nm or more, 0.25 nm or more, 0.5 nm or more, 0.75 nm or more, one nm or more, two nm or more, three nm or more). In some embodiments, the resolution of ion microscope 200 can be from 0.05 nm to 10 nm (e.g., from 0.1 nm to 10 nm, 0.2 nm to 10 nm, 0.25 nm to 3 nm, 0.25 nm to one nm, 0.1 nm to 0.5 nm, 0.1 nm to 0.2 nm). As used herein, the resolution of an ion beam refers to the size of the smallest feature that can be reliably measured from images obtained using the ion microscope. A size of a feature is reliably measured if it can be determined to within an error of 10% or less of the actual size of the feature, and with a standard deviation in the measured size of less than 5% of the actual size of the feature, from ten images of the feature obtained under similar conditions.

In some embodiments, a gas field ion microscope (e.g., He ion microscope) as disclosed herein can be used to distinguish elements in a sample having very close atomic numbers (Z values) using, for example, secondary electron yield, scattered ion abundance, and/or angle- and energy-resolved scattered ion detection. For example, in certain embodiments, the gas field ion microscope can be used to distinguish elements having atomic numbers (Z values) that differ only by one.

In certain embodiments, a gas field ion microscope (e.g., He ion microscope) as disclosed herein can be used to distinguish elements in a sample having a very close masses using, for example, secondary electron yield, scattered ion abundance, and/or angle- and energy-resolved scattered ion detection. In certain embodiments, the gas field ion microscope can be used to distinguish elements having masses that differ by one atomic mass unit or less (e.g., 0.9 atomic mass unit or less, 0.8 atomic mass unit or less, 0.7 atomic mass unit or less, 0.6 atomic mass unit or less, 0.5 atomic mass unit or less, 0.4 atomic mass unit or less, 0.3 atomic mass unit or less, 0.2 atomic mass unit or less, 0.1 atomic mass unit or less). In some embodiments, a sample may have domains formed of materials (e.g., alloys) having different average masses. In such embodiments, the gas field ion microscope can, for example, be used to distinguish domains of material having masses that differ only by one atomic mass unit or less (e.g., 0.9 atomic mass unit or less, 0.8 atomic mass unit or less, 0.7 atomic mass unit or less, 0.6 atomic mass unit or less, 0.5 atomic mass unit or less, 0.4 atomic mass unit or less, 0.3 atomic mass unit or less, 0.2 atomic mass unit or less, 0.1 atomic mass unit or less).

Additional operating parameters that relate to the systems and methods herein as disclosed, for example, by previously-incorporated U.S. patent application Ser. No. 11/600,711 entitled "ION SOURCES, SYSTEMS AND METHODS" by Billy W. Ward et al., filed on Nov. 15, 2006, now published as U.S. Publication No. US 2007/0158558.

Computer Hardware and Software

In general, any of the analysis methods described above can be implemented in computer hardware or software, or a combination of both. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis methods can also be implemented as a computer-readable storage medium, configured with a computer program, where the storage medium so configured causes a computer to operate in a specific and predefined manner to perform the functions described herein.

OTHER EMBODIMENTS

Other embodiments are in the claims.

U.S. patent application Ser. No. 11/600,711, filed on Nov. 15, 2006, the entire contents of which are incorporated herein by reference.

What is claimed is:

1. A method, comprising:
   using a gas field ion source to generate a noble gas ion beam; and
   using the noble gas ion beam to determine dopant information for a sample, the dopant information including dopant concentration as a function of a depth below a surface of the sample, the depth being measured along a direction normal to the surface of the sample,
   wherein determining dopant information comprises measuring one or more images of the sample; and
   wherein at least one of the one or more images is measured by orienting the ion beam so that a central axis of the ion beam forms a non-zero angle relative to the direction normal to the surface of the sample.

2. The method of claim 1, wherein the noble gas comprises helium.

3. The method of claim 1, wherein determining dopant information comprises measuring an abundance of particles leaving the surface of the sample.

4. The method of claim 3, wherein the particles comprise at least one member selected from the group consisting of secondary electrons, scattered noble gas ions, and scattered neutral noble gas atoms.

5. The method of claim 3, wherein determining dopant concentration in the sample comprises comparing the measured abundance of particles to a standard sample to determine the concentration.

6. The method of claim 1, further comprising measuring energies of particles leaving a surface of the sample, angular directions of particles leaving a surface of the sample, or both.

7. The method of claim 6, wherein the particles comprise scattered noble gas ions.

8. The method of claim 1, further comprising determining dopant location information in the sample, and determining a maximum dimension of a doped region of the sample based on the dopant location information.

9. The method of claim 8, wherein determining the maximum dimension comprises determining positions of one or more edges of the doped region.

10. The method of claim 1, wherein the one or more images of the sample comprise multiple images of the sample, and wherein each of the images comprises dopant concentration information.

11. The method of claim 10, wherein each of the multiple images corresponds to a different noble gas ion beam energy.

12. The method of claim 1, further comprising determining a mass of dopant particles.

13. The method of claim 12, wherein determining a mass of dopant particles comprises measuring an energy and an angle of scattered noble gas particles leaving a surface of the sample.

14. The method of claim 12, further comprising determining a composition of the dopant particles based on the mass.

15. The method of claim 13, further comprising determining dopant concentration at a depth below the surface of the sample from the measured energies of scattered noble gas particles.

16. The method of claim 1, further comprising measuring at least one image of the sample, and identifying dopant particles that occupy interstitial sites within a crystal structure of the sample.

17. The method of claim 1, wherein the one or more images comprise multiple images of the sample, wherein each of the multiple images is measured by a charged particle detector, and wherein each of the multiple images corresponds to a different electric potential difference between an electrode of the detector and the sample.

18. The method of claim 1, further comprising exposing the sample to an electron beam during determination of at least some of the dopant information.

19. A method, comprising:

combining data from at least two different images of a sample formed by exposing the sample to a noble gas ion beam, wherein:

a gas field ion source is used to generate the noble gas ion beam;

combining the data provides information including dopant concentration in the sample as a function of a depth below a surface of the sample, the depth being measured along a direction normal to the surface of the sample; and at least one of the at least two different images is measured by orienting the ion beam so that a central axis of the ion beam forms a non-zero angle relative to the direction normal to the surface of the sample.

20. The method of claim 19, wherein a first image of the at least two different images is formed by exposing the sample to noble gas ions at a first ion energy, and a second image of the at least two different images is formed by exposing the sample to noble gas ions at a second ion energy.

21. The method of claim 19, wherein a first image of the at least two different images corresponds to secondary electrons leaving a surface of the sample, and a second image of the at least two different images corresponds to scattered noble gas ions leaving the surface of the sample.

22. A method, comprising:

using a gas field ion source to generate a noble gas ion beam; and comparing reference data for a sample to an image of the sample formed by exposing the sample to the noble gas ion beam to provide information including dopant location in the sample, dopant concentration in the sample, or both, wherein forming the image comprises orienting the ion beam so that a central axis of the ion beam forms a non-zero angle relative to a direction normal to a surface of the sample, and then exposing the sample.

23. A method, comprising:

using a gas field ion source to generate a noble gas ion beam;

exposing a sample to the noble gas ion beam to cause scattered noble gas particles to leave a surface of the sample; and determining dopant information for the sample based on energies of the scattered noble gas particles, wherein:

the dopant information comprises information about a dopant concentration as a function of a depth below a surface of the sample, the depth being measured in a direction normal to the surface of the sample; and wherein exposing the sample comprises orienting the ion beam so that a central axis of the ion beam forms a non-zero angle relative to the direction normal to the surface of the sample, and then exposing the sample to the ion beam.

24. The method of claim 23, wherein the scattered noble gas particles comprise noble gas ions.

25. A method, comprising:

using a gas field ion source to generate a noble gas ion beam;

exposing a sample to the noble gas ion beam to cause scattered noble gas particles to leave a surface of the sample; and determining information about a mass of dopant particles in the sample based on energies of the scattered noble gas particles, angular directions of the scattered noble gas particles, or both, wherein exposing the sample comprises orienting the ion beam so that a central axis of the ion beam forms a non-zero angle relative to a direction normal to the surface of the sample, and then exposing the sample to the ion beam.

26. The method of claim 25, further comprising determining information about masses of a plurality of different dopant particles in the sample based on the energies, the angular directions, or both.

* * * * *

UNITED STATES PATENT AND TRADEMARK OFFICE
CERTIFICATE OF CORRECTION

| | |
|---|---|
| PATENT NO. | : 7,804,068 B2 |
| APPLICATION NO. | : 11/853471 |
| DATED | : September 28, 2010 |
| INVENTOR(S) | : John A. Notte, IV |

It is certified that error appears in the above-identified patent and that said Letters Patent is hereby corrected as shown below:

Title page, Item (56) page 3, Column 2 (Other Publications), Line 29: Delete "Muclear" and insert -- Nuclear --, therefor.

Title page, Item (56) page 3, Column 2 (Other Publications), Line 41: Delete "Intruments" and insert -- Instruments --, therefor.

Title page, Item (56) page 4, Column 1 (Other Publications), Line 15: Delete "Illinoise," and insert -- Illinois, --, therefor.

Title page, Item (56) page 4, Column 1 (Other Publications), Line 28: Delete "Interations" and insert -- Interactions --, therefor.

Title page, Item (56) page 4, Column 1 (Other Publications), Line 41: Delete "Feasiblity" and insert -- Feasibility --, therefor.

Title page, Item (56) page 4, Column 1 (Other Publications), Line 46: Delete "Imagin" and insert -- Imaging --, therefor.

Title page, Item (56) page 4, Column 2 (Other Publications), Line 13: Delete "Interation" and insert -- Interaction --, therefor.

Title page, Item (56) page 4, Column 2 (Other Publications), Line 14: Delete "Abastract" and insert -- Abstract --, therefor.

Title page, Item (56) page 4, Column 2 (Other Publications), Lines 16-17: Delete "Tehcnology" and insert -- Technology --, therefor.

Title page, Item (56) page 4, Column 2 (Other Publications), Line 48: Delete "microsopc" and insert -- microscope --, therefor.

Signed and Sealed this
Twenty-eighth Day of December, 2010

David J. Kappos
*Director of the United States Patent and Trademark Office*

Column 37, Line 57: After "measured" insert -- . -- .